(12) United States Patent
Singer et al.

(10) Patent No.: US 9,273,022 B2
(45) Date of Patent: Mar. 1, 2016

(54) PROCESS FOR THE SYNTHESIS OF 4,5,6,7-TETRACHLORO-3',6'-DIHYDROXY-2', 4', 5'7'-TETRAIODO-3H-SPIRO[ISOBENZOFURAN-1,9'-XANTHEN]-3-ONE (ROSE BENGAL) AND RELATED XANTHENES

(71) Applicant: Provectus Pharmaceuticals, Inc., Knoxville, TN (US)

(72) Inventors: Jamie Singer, Knoxville, TN (US); Eric A. Wachter, Oak Ridge, TN (US); Timothy Scott, Knoxville, TN (US); Marlon Lutz, Chicago, IL (US); Kevin Babiak, Evanston, IL (US); Sahadeva Reddy Damireddi, Waverly, IA (US); J. Robert Durrwachter, Charles City, IA (US)

(73) Assignee: Provectus Pharmaceuticals, Inc., Knoxville, TN (US)

( * ) Notice: Subject to any disclaimer, the term of this patent is extended or adjusted under 35 U.S.C. 154(b) by 0 days.

(21) Appl. No.: 14/447,063

(22) Filed: Jul. 30, 2014

(65) Prior Publication Data

US 2014/0343296 A1 Nov. 20, 2014

Related U.S. Application Data

(60) Continuation-in-part of application No. 13/916,408, filed on Jun. 12, 2013, which is a division of application No. 12/884,833, filed on Sep. 17, 2010, now Pat. No. 8,530,675.

(60) Provisional application No. 61/243,701, filed on Sep. 18, 2009.

(51) Int. Cl.
*C07D 311/82* (2006.01)
*C07D 493/10* (2006.01)

(52) U.S. Cl.
CPC ............ *C07D 311/82* (2013.01); *C07D 493/10* (2013.01)

(58) Field of Classification Search
CPC ............................ C07D 311/82; C07D 493/10
USPC ........................................................... 549/223
See application file for complete search history.

(56) References Cited

U.S. PATENT DOCUMENTS

| 1,931,049 A | 10/1933 | Woods et al. |
| 1,965,842 A | 7/1934 | Kranz et al. |

(Continued)

FOREIGN PATENT DOCUMENTS

| CN | 1331797 A | 1/2002 |
| CZ | 124483 | 1/1966 |

(Continued)

OTHER PUBLICATIONS

CAS Record for patent CZ 124483.

(Continued)

*Primary Examiner* — T. Victor Oh
(74) *Attorney, Agent, or Firm* — Husch Blackwell LLP

(57) ABSTRACT

A new process for the manufacture of iodinated xanthenes in high purity includes a cyclization step followed by an iodination step. No extraction, chromatographic or solvent concentration steps are required, and the intermediate as well as final compounds are isolated via filtration or similar means. The process requires a single organic solvent, and the steps are completed at temperatures below 100° C. The exclusion of chloride ions, of chloride free-radicals, hypochlorite ions, or hypochlorous acid as reagents or from reagents that may generate these species in situ in the presence of oxidants, prevents undesirable impurity formation. Several new compounds have been conceived and isolated using these methods. These new compounds are also formed into new medicaments.

55 Claims, 3 Drawing Sheets

(56) References Cited

U.S. PATENT DOCUMENTS

| | | | |
|---|---|---|---|
| 5,637,733 | A | 6/1997 | Sujeeth |
| 6,162,931 | A | 12/2000 | Gee et al. |
| 6,649,769 | B2 | 11/2003 | Lee et al. |
| 6,800,765 | B2 | 10/2004 | Diwu et al. |
| 7,279,264 | B2 | 10/2007 | Cheon et al. |
| 7,518,002 | B2 | 4/2009 | Tran-Guyon et al. |
| 2007/0292352 | A1 | 12/2007 | Marnett et al. |
| 2008/0061289 | A1 | 3/2008 | Volpe et al. |

FOREIGN PATENT DOCUMENTS

| | | |
|---|---|---|
| DE | 108838 | 2/1899 |
| EP | 0 050 684 A1 | 5/1982 |
| ES | 8606451 | 10/1985 |
| IN | 168346 | 12/1988 |
| JP | 11-508277 | 7/1999 |
| RU | 517222 A1 | 6/1977 |
| RU | 792878 A1 | 2/1982 |
| RU | 992516 A1 | 1/1983 |
| WO | WO 97/39064 | 10/1997 |
| WO | WO 02/05812 A1 | 1/2002 |
| WO | WO 02/062333 A1 | 8/2002 |
| WO | WO 2008/003954 A1 | 1/2008 |

OTHER PUBLICATIONS

Arnold, J.T. et al, "Hypochlorite-Induced Substitution of Chlorine for Bromine in Aromatic Compounds" J. Org. Chem., vol. 57, No. 1, 1992, pp. 391-393.
Baeyer, A., "Flourescein and Fluorescin," Chemische Berichte, vol. 4, 1871, pp. 555-558 (with English translation of relevant section).
Bayraktaroglu, T.O. et al, "Hypochlorite-Induced Substitution of Chlorine for Iodine in Aromatic Compounds and the Role of Iodyl Intermediates," J. Org. Chem., vol. 58 No. 5, 1993, pp. 1264-1265.
Bindschedler, M.M. et al, Tetraiodofruorescene Sodium, Le Moniteur Scientifique: Journal des Science Pures Et Appliquees, vol. 8, 1878, pp. 1169-1172 (with English translation of relevant section).
21 CFR Ch. I, §74.303, FD&C Red No. 3, Apr. 1, 2008, p. 392.
Grabe, C., "Ueber Tetrachlorphtalsaeure," Justus Liebigs Armalen der Chemie, vol. 238, 1887, pp. 318-338 (with English translation of relevant section).
Hallaba, E. et al, "Production of Labelled Rose Bengale with $I_{131}$," Isotopenpraxis, vol. 2, 1966, pp. 194-196.
Jagannathan, E. et al, "Electrochemical Preparation of Erythrosin and Eosin," Electrochemicals, vol. 3, No. 1, Jan.-Feb. 1987, pp. 29-31.
Kamikura, M., "Intermediates and Side Reaction Products in Food Red No. 3 (Erythrosine)," Journal of the Food Hygienic Society of Japan, Shokuhin Eiseigaku Zasshi, 1985, vol. 26, No. 3, pp. 243-252.
Kimura, M., "Spirolactones of Xanthene. III. Formation and Molecular Structure of Novel Spirolactones of Xanthene and Dibenzo[c,h]xanthene," J. Heterocyclic Chem., vol. 24, Jan.-Feb. 1987, pp. 283-288.
Le Royer, A., "Dichloroflourescein and Tetraiododichlorofluorescein," Annalen der Chemie, vol. 238, 1887, pp. 350-361.
McCullagh, J.V. et al, "Synthesis of Triarylmethane and Xanthene Dyes Using Electrophilic Aromatic Substitution Reactions with supplementary material," Journal of Chemical Education, vol. 84, No. 11, Nov. 2007, pp. 1799-1802.
Lamberts, J.J.M. et al, "Novel Rose Bengal Derivatives: Synthesis and Quantum Yield Studies," Journal of the American Chemical Society, vol. 106, No. 20, 1984, pp. 5879-5883.
Pratt, D.S. et al, "Phthalic Acid Derivatives; Constitution and Color. XVII., Tetrabromo-Fluorescein, Tetrabromoeosin and Some of Their Derivatives," JACS, vol. 41, May 31, 1919, pp. 1293-1297.
Pratt, D.S. et al, "Phthalic Acid Derivatives; Constitution and Color. XI. Phenoltetraiodophthalein and Some of Its Derivatives," JACS, vol. 40, Oct. 17, 1917, pp. 254-264.
Pukirev, A., "Preparation and Purification of Iodeosin and Erythrosin," Khim. Farm. Prom., vol. 2, 1933, pp. 58-63 (English Abstract only).
Rose Bengal Reagent, USP XXII, 1990, pp. 1716-1717; p. 1766 and p. 1799.
Wada, K. et al, "Monitoring of the Generation of Non-Mutagenic Benzoic Acid Compounds During the Manufacture of Erythrosine," Food Additives and Contaminants, vol. 21, No. 12, Dec. 2004, pp. 1137-1148.
Zakrzewski, A. et al, "Bleaching Pruducts of Rose Bengal Under Reducing Conditions," Tetrahedron, vol. 43, No. 20, 1987, pp. 4507-4512.
Sun, W.-C., et al, "Synthesis of Fluorinated Fluoresceins," J. Org. Chem., vol. 62, No. 19, 1997, pp. 6469-6475.
International Preliminary Report of Patentability re counterpart International application No. PCT/US2010/049341, dated Mar. 20, 2012.
Lamberts, J.J.M. et al, "Rose Bengal Derivatives as Singlet Oxygen Sensitizers," Tetrahedron, vol. 41, No. 11, Jan. 1, 1985, pp. 2183-2190.
Search Report re European application No. EP 10817918.5, dated Feb. 26, 2013.
Office Action re Chinese application No. CN 201080041506.7, dated May 22, 2013 (with English translation).

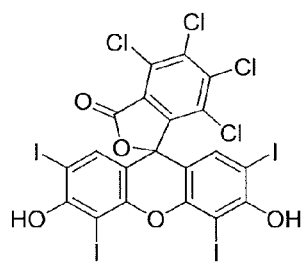
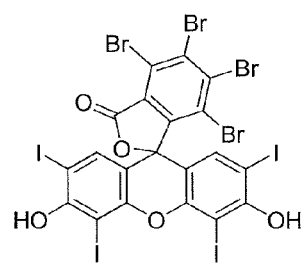
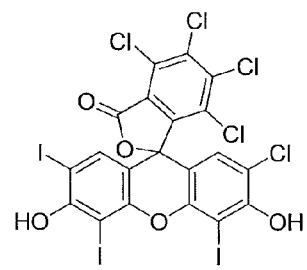
Figure 1a          Figure 1b          Figure 1c
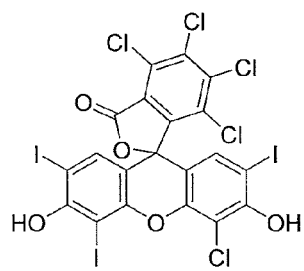
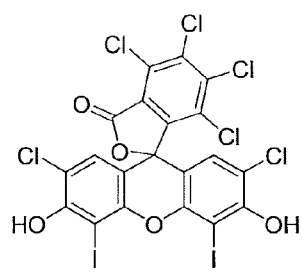
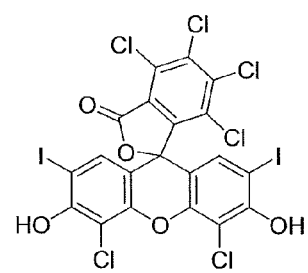
Figure 1d          Figure 1e          Figure 1f
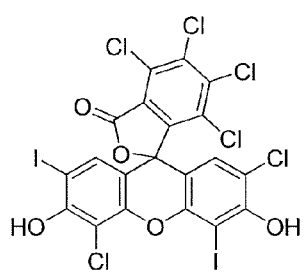
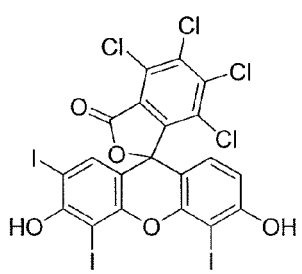
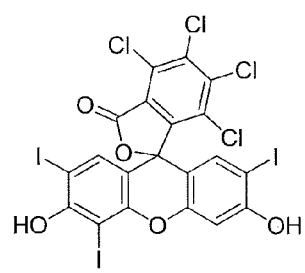
Figure 1g          Figure 1h          Figure 1i

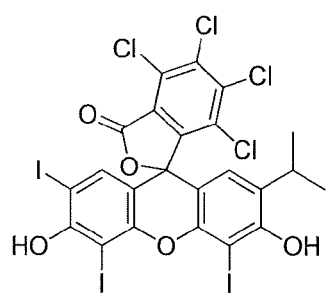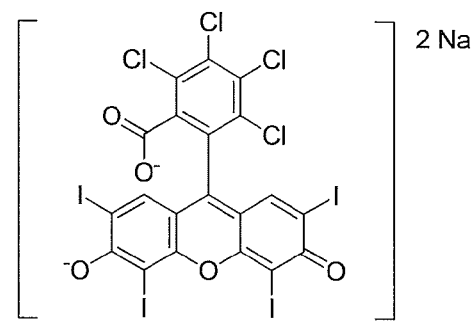
Figure 1s                    Figure 1t

PROCESS FOR THE SYNTHESIS OF 4,5,6,7-TETRACHLORO-3',6'-DIHYDROXY-2',4',5'7'-TETRAIODO-3H-SPIRO[ISOBENZOFURAN-1,9'-XANTHEN]-3-ONE (ROSE BENGAL) AND RELATED XANTHENES

CROSS-REFERENCE TO RELATED APPLICATION

This application is a continuation-in-part of copending U.S. application Ser. No. 13/916,408, filed on Jun. 12, 2013 which is a divisional of U.S. application Ser. No. 12/884,833, filed on Sep. 7, 2010 (now U.S. Pat. No. 8,530,675 issued Sep. 10, 2013) which claims benefit from provisional application Ser. No. 61/243,701 filed on Sep. 18, 2009, which are all incorporated herein by reference.

FIELD OF THE INVENTION

The present invention relates to methods of preparation or synthesis and isolation of highly purified Rose Bengal, Rose Bengal Lactone and related xanthenes, and also relates to highly purified Rose Bengal, Rose Bengal Lactone and related xanthenes. One aspect of the present invention relates to synthetic procedures to prepare iodinated fluorescein derivatives that contain at most 2% by weight, and preferably less than 0.15% by weight, of individual organic impurities. Controlling impurities to the 0.15% or 1500 ppm level or lower is relevant for pharmaceutical utility since this represents the qualification threshold for compliance with International Conference of Harmonisation (ICH) guidelines. Hence, another aspect of this invention relates to the pharmaceutical utility and identification of the novel compounds that are disclosed herein, for which the above synthesis was specifically engineered to control their formation.

BACKGROUND OF THE INVENTION

The fluorescein structural motif and one step cyclization from phthalic anhydride and resorcinol is believed to have been first described in 1871 by Baeyer (*Berichte.* 1871: 4, 555). Graebe (*Annalen.* 1887: 18, 318) is believed to be the first to use halogenated phthalic anhydride as substrates in the cyclization noting in his report the use of an excess of anhydride (1.3 equivalents) to resorcinol. Iodination of dichlorofluorescein appeared in the literature in 1887 with a report by Le Royer (*Annalen.* 1887: 238, 359). In the 20$^{th}$ century, several uses for fluorescein analogs emerged. The compounds have been used as textile dyes, biological stains, building blocks for non-volatile memory devices, thermoimaging substrates and food and cosmetics coloring. For example, erythrosine (FD&C No. 3) and partially iodinated erythrosine (D&C Nos. 11 and 12) are used as food, drug and cosmetic dyes. A particular tetraiodo-xanthene, Rose Bengal, has been used for visualization of ocular disease and, in radiolabeled form, as a medical diagnostic for liver function, appearing in the United States Pharmacopeia in 1965.

The cyclization, however, to create the xanthene core of Rose Bengal has not substantially improved from the 1880's technology (high temperature melts in open kettles), even though interest in the synthesis of the non-halogenated analogs and elaboration on the fluorescein motif is extensive. The known synthetic methods produce a range of unpredictable and poorly characterized impurities including residual solvents, inorganic compounds and organic compounds derived from side reactions or degradation processes. For many historical uses in industrial applications, food dyes or diagnostics, these impurities are permissible. For example, the United States Code of Federal Regulations (CFR) allows an impurity level for FD&C No. 3 (erythrosine) of no more than 1% mono-iodinated impurities and no more than 9% of other lower iodinated fluoresceins. The CFR also allows residual impurities originating in the cyclization step, such as partially iodinated phthalic acids and resorcinols (for example, see: Kamikura, *Shokuhin Eiseigaku Zasshi* 1985: 26, 243 and Wada et al., *Food. Add. Contam.* 2004: 21, 1137).

Such historical coloring agent specifications are quite disparate to modern International Conference of Harmonisation (ICH) guidelines for a new drug substance, which requires reporting of impurities of 0.05% or higher, comprehensive identification of any organic impurity present at levels of 0.1% or higher, and thorough toxicologic qualification of any impurities over 0.15%, and further provide limits on inorganic impurities and especially stringent limits on residual solvents. Hence, when introducing this class of compounds into the body at therapeutic doses, the necessity to have a well controlled, predictable and reproducible synthesis becomes a priority. Unpredictable generation of multiple impurities during synthetic steps or in purification is not an option for inclusion in such a specification, especially with a potential parenteral drug product formulation.

To make reagent grade Rose Bengal, the United States Pharmacopeia XXII recommends using HCl to purify Rose Bengal via an acid/base manipulation. The present inventors have found that, quite surprisingly, when oxidants like hydrogen peroxide or oxone are present, treatment of iodinated fluoresceins with reagents that contain or can generate aqueous chloride ions causes a side reaction where one or more of the I substituents can be transhalogenated to Cl. This can also occur when chloride free radicals, hypochlorite ion, or hypochlorous acid are present. This side reaction during the preparation of Rose Bengal has not been reported previously and the cyclization step, the iodination step and any purification scheme must be carefully controlled to prevent this undesirable side reaction.

While iodinated fluorescein analogs have been previously described and often generically recite the word "halogen", none of these prior disclosures appear to enable the synthesis of iodo-xanthene substituted fluoresceins directly from iodo-resorcinols. Also, none of the prior disclosures appear to require at least one iodine to be present in the molecule, and none claim a pharmaceutical applicability of these compounds that is most certainly iodine dependent. Predominant use of fluoresceins for nontherapeutic purposes have resulted in a paucity of information regarding the description and reduction to practice of methods required for the preparation of high purity active pharmaceutical ingredients in this compound class, as well as methods for the identification, characterization and synthesis of minor by-products which may have utility as human therapeutics or as colorants. Iodinated xanthenes have been generically included as embodiments in various disclosures, and Rose Bengal is a well known compound first described in the 1880's. None of these references, however, has described the isolation or identification, nor disclosed or indicated the possibility of the existence of, the transhalogenated minor products composed of at least one I and at least one Cl substituent on the xanthene core. The present inventors have discovered that these products can exist in up to 2% by weight in commercial samples of Rose Bengal. Furthermore, prior references allude to lower iodinated xanthene contaminants (for example, not more than 9% is allowed for the dye certification of erythrosine in the present CFR 74.303), but none of these references have proposed a structure or a name for triiodinated versions that can be substituted with hydrogen in either the 2' or 4' position or their corresponding atropisomers (see FIGS. 1q and 1r infra and refer to U.S. Pat. No. 6,649,769 for a discussion of atropisomerism on this scaffold). Nor has the prior references taught or suggested the isolation or enabled the synthesis of independent I/Cl substitutions about the xanthene core. The present invention identifies, characterizes and establishes methods to efficiently control the synthesis of these by-products to meet the standards required for utility in pharmaceutical applications. In addition, the process of the present invention avoids undesirable formation of these by-products, avoids the necessity of using multiple solvents and sets strict control of reagents, all of which improve handling, yield, purity and applicability of the process for pharmaceutical use.

SUMMARY OF THE INVENTION

The present invention relates to materials and methods to control the impurity level in iodinated xanthenes of Formula 3 and Formula 4 manufactured for pharmaceutical use, processes for the manufacture of these iodinated xanthene compounds, and the disclosure of related but previously unanticipated transhalogenated impurities. The present invention also relates to materials and methods for preparing the same, and in particular processes for preparing erythrosine (FD&C 3), Rose Bengal, and other related iodinated xanthenes in purity suitable for pharmaceutical use. In one embodiment, this process employs only a single organic solvent, low temperature (less than 100° C.) and requires use of very limited and select additives and modifiers to avoid formation of impurities. Avoiding formation of transhalogented impurities can, for example, be accomplished by limiting chloride ion to less than 1500 ppm in the reaction mixtures, and especially in the reaction mixtures during the iodination step. No extraction, chromatographic or solvent concentration steps are required, and the intermediate, as well as final compounds, can be isolated via filtration or similar means. The present invention is also directed to specific analogs and new compounds, particularly those that can be made or are avoided via the method disclosed above. These compounds have been isolated and identified, and are adapted for pharmaceutical, medicinal, cosmetic and colorant use.

In a further embodiment, there is provided a process for the preparation of a compound of Formula 3,

FORMULA 3

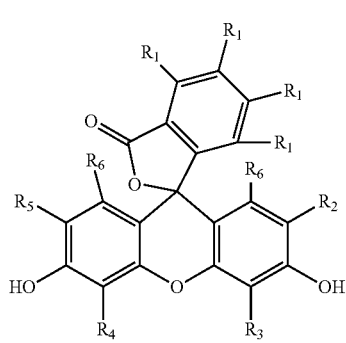

in which each position $R_1$ is independently $C_1$-$C_4$ alkyl, halogen or H; and $R_2$, $R_3$, $R_4$ and $R_5$ are independently I, F, Cl, $C_1$-$C_4$ alkyl or H, where at least one of $R_2$, $R_3$, $R_4$ or $R_5$ is I, and each position $R_6$ is independently H or $C_1$-$C_4$ alkyl; comprising reacting a compound of Formula 3 in which each position $R_1$ is independently $C_1$-$C_4$ alkyl, halogen or H; $R_2$, $R_3$, $R_4$ and $R_5$ are independently F, Cl, $C_1$-$C_4$ alkyl or H and at least one of $R_2$, $R_3$, $R_4$ or $R_5$ is H with iodine ($I_2$) in the presence of aqueous base to replace at least one of $R_2$, $R_3$, $R_4$ or $R_5$ with I.

Another embodiment is directed to a method of making a compound of Formula 3 in which each position $R_1$ is independently $C_1$-$C_4$ alkyl, halogen or H; $R_2$, $R_3$, $R_4$ and $R_5$ are independently halogen, $C_1$-$C_4$ alkyl or H; and each position $R_6$ is independently H or $C_1$-$C_4$ alkyl; comprising reacting a compound of Formula 1 or Formula 1a,

FORMULA 1

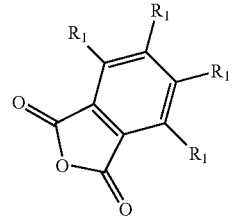

FORMULA 1a

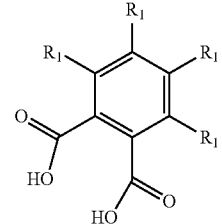

in which each of position $R_1$ is independently halogen, $C_1$-$C_4$ alkyl or H, with a compound of Formula 2

FORMULA 2

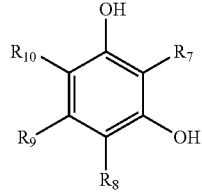

in which $R_7$, $R_8$, $R_{10}$ are independently F, Cl, $C_1$-$C_4$ alkyl or H; and $R_9$ is H.

A further embodiment is directed to a method of making derivatives of Formula 3 in which each position $R_1$ is independently halogen or H; $R_2$, $R_3$, $R_4$ and $R_5$ are independently I, Br, Cl, F or H, where at least one of $R_2$, $R_3$, $R_4$ and $R_5$ is Cl; and $R_6$ is H; comprising reacting the compound of Formula 3 with a chlorine radical, chloride ion or chloride ion generated in situ (i.e., such as a sodium hypochlorite solution, or hypochlorous acid) such that any $R_1$, $R_2$, $R_3$, $R_4$ or $R_5$ that is I or Br can be independently replaced by Cl.

Another embodiment relates to compounds of Formula 3 where at least one, but no more than two, positions selected from $R_2$, $R_3$, $R_4$ or $R_5$ is Cl and each position $R_1$ is independently Br, F, Cl or I; provided that any $R_2$, $R_3$, $R_4$ or $R_5$ that isn't Cl or H is I and each position $R_6$ is independently H or $C_1$-$C_4$ alkyl.

The compounds of Formula 3 described herein have properties useful in the pharmaceutical, medicinal, cosmetic and colorant industries. Accordingly, the present invention also relates to the claimed compounds in medicaments for topical or intracorporeal application, including as an active substance in medicaments for chemotherapeutic or photodynamic treatment of human or animal disease.

The compounds of Formula 3, methods for their production, medicaments and uses so defined herein shall include all forms of such compounds that have been saponified or otherwise reacted to convert such compounds from their lactone form (Formula 3) to their quinoid form, (Formula 4), where $R_{11}$ and $R_{12}$ are independently H or Na, K, Li or another counter-ion capable of forming a salt.

FORMULA 4

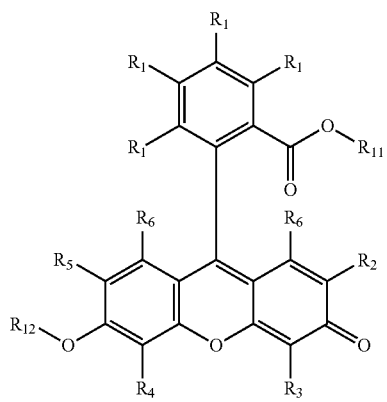

In a further embodiment, the present invention relates to a method for the preparation of a compound of Formula 4 in which $R_1$ is independently Cl or Br, $R_2$, $R_3$, $R_4$ and $R_5$ are I, and $R_6$ is H. Combining a compound of Formula 3a in which $R_1$ is independently Cl or Br, and $R_2$, $R_3$, $R_4$, $R_5$ and $R_6$ are H, with iodide in a solution substantially free of chloride ions to form a compound of Formula 4 in which $R_1$ is independently Cl or Br, $R_2$, $R_3$, $R_4$ and $R_5$ are I, and $R_6$ is H, affords substantive improvement over prior methods for preparation of a compound of Formula 4, the improvement comprising a substantial nonexistence of transhalogenated derivatives of the compound of Formula 4 where $R_1$ is independently Cl or Br, at least one of $R_2$, $R_3$, $R_4$ and $R_5$ is Cl and any $R_2$, $R_3$, $R_4$ and $R_5$ that is not Cl is I, and where $R_6$ is H.

In a further embodiment, the present invention relates to a method for the preparation of a compound of Formula 3,

FORMULA 3

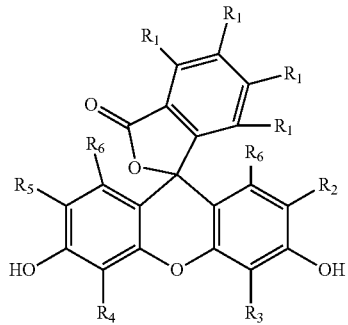

in which $R_1$ is independently Cl or Br; $R_2$, $R_3$, $R_4$ and $R_5$ are I; and $R_6$ is H, comprising Step 1: combining a compound of Formula 1 or Formula 1a,

FORMULA 1

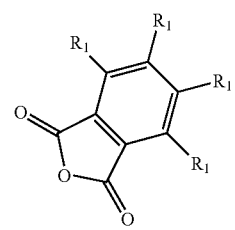

FORMULA 1a

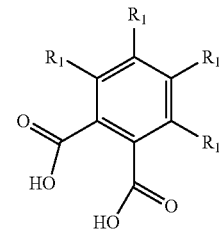

in which $R_1$ is independently Cl or Br, with about two equivalents of a compound of Formula 2,

FORMULA 2

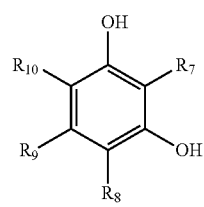

in which $R_7$, $R_8$, $R_9$ and $R_{10}$ are H, in an acidic solution;
  mixing together at temperatures ranging from 20° C. to 250° C., and preferably at a temperature of 85° C.-95° C.; and
  isolating the resultant cyclized intermediate product of the Formula 3a.

FORMULA 3a

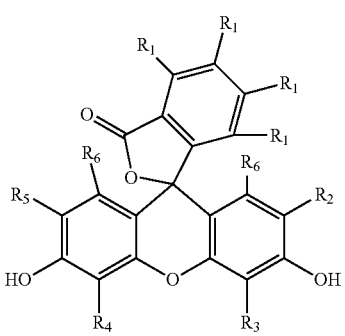

in which $R_1$ is independently Cl or Br and $R_2$, $R_3$, $R_4$, $R_5$ and $R_6$ are H; followed by
  Step 2: combining said intermediate of Formula 3a with a chloride-ion-free aqueous solution;
  treating said solution of intermediate of Formula 3a with iodine ($I_2$), and mixing at temperatures ranging from 20° C. to 100° C. for a time such that conversion to Formula 3 is substantially complete, for example as determined by HPLC or similar means;

quenching the reaction mixture containing Formula 3 with a chloride-ion-free iodine scavenger;

acidifying said quenched reaction mixture with a chloride-ion-free acidic solution to pH less than 5; and isolating said final product of Formula 3.

It is further preferred in the above method for the preparation of a compound of Formula 3 that the acidic solution of Step 1 in which the compounds of Formula 1 or Formula 1a and Formula 2 are combined is free or substantially free of chloride ions and free or substantially free of reagents which can produce chloride ions in the reaction mixture.

It is also further preferred in the above method for the preparation of a compound of Formula 3 that the intermediate of Formula 3a in Step 2 is free or substantially free of chloride ions and free or substantially free of reagents or other impurities which can produce chloride ions in the reaction mixture.

It is also further preferred in the above method for the preparation of a compound of Formula 3 that the solution in which the intermediate of Formula 3a and iodine are combined has a basic pH.

In a variation on the above method for the preparation of a compound of Formula 3, Step 1 of the method for the preparation of a compound of Formula 3 may comprise combining a compound of Formula 1 or Formula 1a with less than two equivalents of a compound of Formula 2. This embodiment is less preferred since the yield of Formula 3 will be lower yield than that provided using the stoichiometry of preferred embodiment.

In another further embodiment, the present invention relates to a method for the preparation of a compound of Formula 3,

FORMULA 3

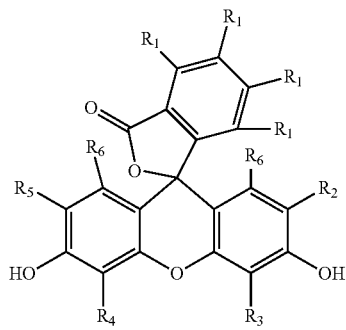

in which $R_1$ is independently I, Br, Cl, F, $C_1$-$C_4$ alkyl or H, and $R_2$, $R_3$, $R_4$ and $R_5$ are independently I, F, Cl, $C_1$-$C_4$ alkyl or H, where at least any one but no more than three of $R_2$, $R_3$, $R_4$ or $R_5$ is I, comprising:

Step 1: combining a compound of Formula 1 or Formula 1a,

FORMULA 1

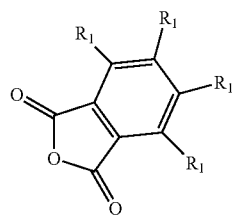

FORMULA 1a

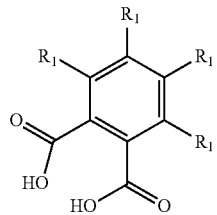

in which $R_1$ is independently I, Br, Cl, F, $C_1$-$C_4$ alkyl or H with a compound of Formula 2

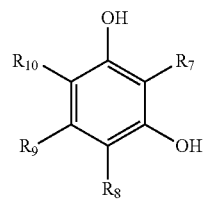

in which $R_7$, $R_8$, and $R_{10}$ are independently F, Cl, H, or $C_1$-$C_4$ alkyl and at least two of $R_7$, $R_8$ or $R_{10}$ are H and $R_9$ is H;

in an acidic solution free or substantially free of chloride ions and free or substantially free of reagents or impurities which can produce chloride ions in the reaction mixture;

mixing together at temperatures ranging from 20° C. to 250° C.;

isolating the resultant cyclized intermediate product of Formula 3a, for example by filtration or similar means; followed by FORMULA 3a

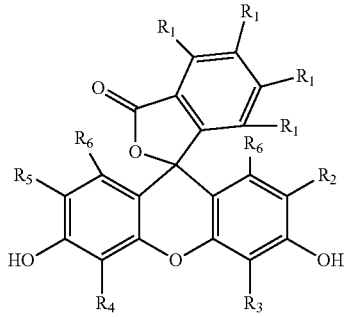

Step 2: combining said intermediate of Formula 3a which is free or substantially free of chloride ions and free or substantially free of impurities or impurities which can produce chloride ions with a chloride-ion-free or substantially chloride-ion-free aqueous solution;

treating said aqueous solution of intermediate of Formula 3a with iodine ($I_2$);

mixing at temperatures ranging from 20° C. to 100° C. for a sufficient time such that conversion to Formula 3 is substantially complete, for example as determined by HPLC or similar means;

quenching the reaction mixture containing Formula 3 with a chloride-ion-free iodine scavenger;

acidifying said quenched reaction mixture with a chloride-ion-free acidic solution to pH<5; and isolating said final product by filtration or similar means.

It is preferred in the above method for the preparation of a compound of Formula 3 that the aqueous solution of Step 2 in which the intermediate of Formula 3a and iodine are combined has a basic pH.

It is further preferred that the mixing of Step 2 be continued for sufficient time such that conversion to Formula 3 is at least 90%, and more preferably at least 95%, and most preferably at least 98% complete, such time generally being in the range of about 1 to 24 hours, and more preferably from about 2 to 18 hours.

In another embodiment, the present invention relates to a compound of Formula 4 in which $R_1$ is independently F, Cl, Br, I, H or $C_1$-$C_4$ alkyl; $R_2$, $R_3$, $R_4$, and $R_5$ are independently Cl, H or I with at least one substituent selected from $R_2$, $R_3$, $R_4$, $R_5$ is I and at least one other substituent is Cl or H; and $R_6$ is independently H or $C_1$-$C_4$ alkyl; and all (a) tautomeric forms, (b) atropisomers, (c) closed lactone forms as depicted in Formula 3, (d) enantiomers of the lactone forms depicted in Formula 3, and (e) pharmaceutically acceptable salts thereof.

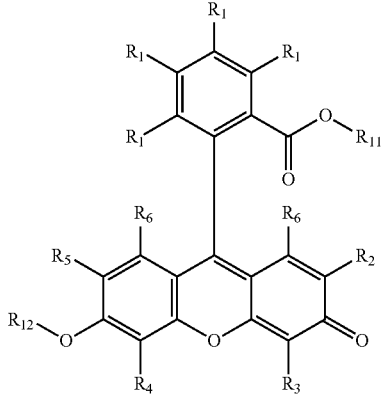

FORMULA 4

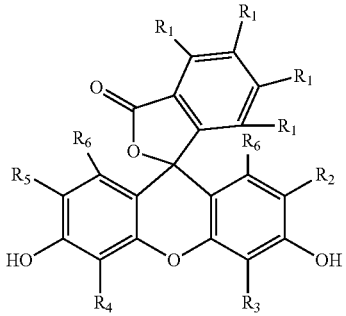

FORMULA 3

BRIEF DESCRIPTION OF THE DRAWINGS

FIG. 1a is an illustration of 4,5,6,7-tetrachloro-3',6'-dihydroxy-2',4',5',7'-tetraiodo-3H-spiro[isobenzofuran-1,9'-xanthen]-3-one, also named 4,5,6,7-tetrachloro-2',4',5',7'-tetraiodofluorescein or Rose Bengal Lactone;

FIG. 1b is an illustration of 4,5,6,7-tetrabromo-3',6'-dihydroxy-2',4',5',7'-tetraiodo-3H-spiro[isobenzofuran-1,9'-xanthen]-3-one, also named 4,5,6,7-tetrabromo-2',4',5',7'-tetraiodofluorescein;

FIG. 1c is an illustration of 2',4,5,6,7-pentachloro-3',6'-dihydroxy-4',5',7'-triiodo-3H-spiro[isobenzofuran-1,9'-xanthen]-3-one, also named 2',4,5,6,7-pentachloro-4',5',7'-triiodofluorescein;

FIG. 1d is an illustration of 4,4',5,6,7-pentachloro-3',6'-dihydroxy-2',5',7'-triiodo-3H-spiro[isobenzofuran-1,9'-xanthen]-3-one, also named 4,4',5,6,7-pentachloro-2',5',7'-triiodofluorescein;

FIG. 1e is an illustration of 2',4,5,6,7,7'-hexachloro-3',6'-dihydroxy-4',5'-diiodo-3H-spiro[isobenzofuran-1,9'-xanthen]-3-one, also named 2',4,5,6,7,7'-hexachloro-4',5'-diiodofluorescein;

FIG. 1f is an illustration of 4,4',5,5',6,7-hexachloro-3',6'-dihydroxy-2',7'-diiodo-3H-spiro[isobenzofuran-1,9'-xanthen]-3-one, also named 4,4',5,5',6,7-hexachloro-2',7'-diiodofluorescein;

FIG. 1g is an illustration of 2',4,5,5',6,7-hexachloro-3',6'-dihydroxy-4',7'-diiodo-3H-spiro[isobenzofuran-1,9'-xanthen]-3-one, also named 2',4,5,5',6,7-hexachloro-4',7'-diiodofluorescein;

FIG. 1h is an illustration of 4,5,6,7-tetrachloro-3',6'-dihydroxy-2',4',5'-triiodo-3H-spiro[isobenzofuran-1,9'-xanthen]-3-one, also named 4,5,6,7-tetrachloro-2',4',5'-triiodofluorescein;

FIG. 1i is an illustration of 4,5,6,7-tetrachloro-3',6'-dihydroxy-2',4',7'-triiodo-3H-spiro[isobenzofuran-1,9'-xanthen]-3-one, also named 4,5,6,7-tetrachloro-2',4',7'-triiodofluorescein;

FIG. 1s is an illustration of 4,5,6,7-tetrachloro-3',6'-dihydroxy-2',4',5'-triiodo-7'-isopropyl-3H-spiro[isobenzofuran-1,9'-xanthen]-3-one, also named 7'-isopropyl-4,5,6,7-tetrachloro-2',4',5'-triiodofluorescein.

FIG. 1t is an illustration of 2,3,4,5-tetrachloro-6-(6-hydroxy-2,4,5,7-tetraiodo-3-oxo-3H-xanthen-9-yl)benzoic acid disodium salt, also named 4,5,6,7-tetrachloro-2',4',5',7'-tetraiodofluorescein disodium or Rose Bengal.

DETAILED DESCRIPTION OF THE PRESENTLY PREFERRED EMBODIMENTS

Definitions

Figure 1J:
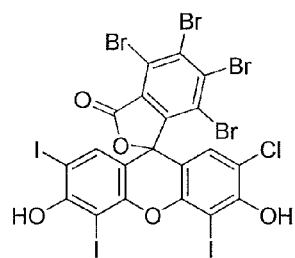
FIG. 1j is an illustration of 4,5,6,7-tetrabromo-2'-chloro-3',6'-dihydroxy-4',5',7'-triiodo-3H-spiro[isobenzofuran-1,9'-xanthen]-3-one, also named 2'-chloro-4,5,6,7-tetrabromo-4',5',7'-triiodofluorescein.

"$C_1$-$C_4$ alkyl" refers to straight chain and branched saturated or unsaturated hydrocarbon groups, generally having a specified number of carbon atoms. Examples of $C_1$-$C_4$ alkyl groups include, without limitation, methyl, ethyl, n-propyl, i-propyl, n-butyl, s-butyl, i-butyl and t-butyl.

"Halo" and "halogen" may be used interchangeably, and refer to fluoro, chloro, bromo, and iodo functionalities.

"Substantially chloride free" and similar language refers to reaction conditions, reagents or intermediates that are free of chloride ion, impurities containing chloride ion, or impurities which can produce chloride ion, to a level of purity sufficient to avoid undesirable formation of transhalogenated impurities of Formula 3, Formula 3a or Formula 4 at levels of 0.15% (e.g., 1500 ppm) or greater, or wherein such reaction conditions, reagents or intermediates contain chloride ion, impurities containing chloride ion, or impurities which can produce chloride ion at a level of 1500 ppm or lower.

"Substantially free of transhalogenated impurities" and similar language refers to the presence of compounds of Formula 3, and Formula 4 wherein, $R_1$ is independently Cl or Br, at least one of $R_2$, $R_3$, $R_4$ and $R_5$ is Cl and the remainder are I, and $R_6$ is H, at a level of 0.15% (e.g., 1500 ppm) or lower.

Generic Structural Representations

The structures of various intermediate and final products of Formula 3, Formula 3a, Formula 3b and Formula 4 are illustrated for the sake of simplicity in their generic lactone or quinoid isomeric forms, and may, depending upon pH or other conditions, be present in their alternate isomeric faun (e.g., quinoid instead of lactone, or lactone instead of quinoid). Such generic representation is not intended to limit the disclosure to the specific generic isomeric forms illustrated.

Reaction Schemes

Scheme I shows one embodiment of the present invention which involves a method of making iodinated xanthenes (such as, for example, Formula 3). This method includes reacting a phthalic anhydride (Formula 1) or a di-acid (Formula 1a) with an excess of a resorcinol (Formula 2) to give a compound of Formula 3a where $R_2$, $R_3$, $R_4$, $R_5$ and $R_6$ are not I and at least one of $R_2$-$R_5$ is H. This compound, following minimal isolation, is then subjected to iodination to give a compound of Formula 3 where at least one of $R_2$, $R_3$, $R_4$ or $R_5$ is substituted with I.

SCHEME I

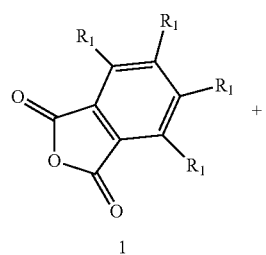

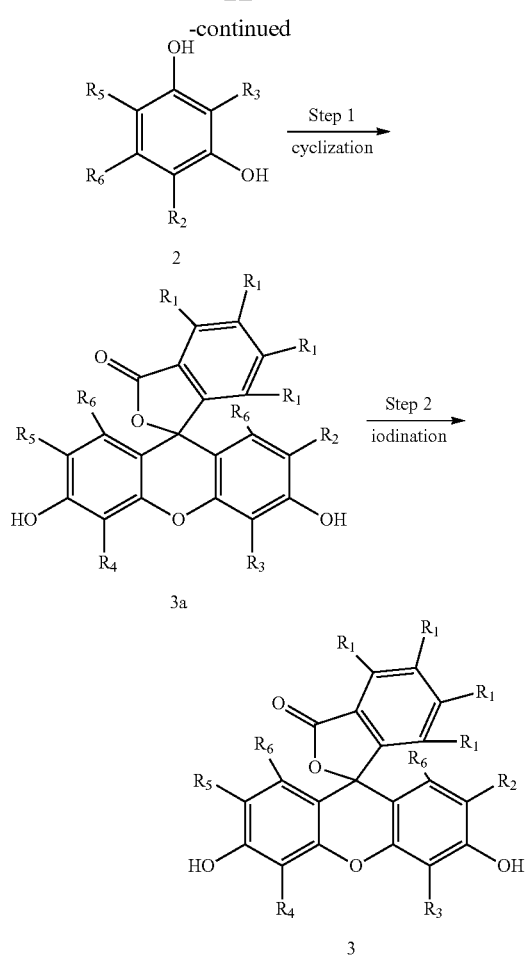

The cyclization reaction, Step 1 above, may be carried out, for example, using neat to 10% methanesulfonic acid (MSA) in water, at temperatures from 0° C. to reflux. As either Formula 1 or Formula 1a undergoes protonation in the presence of acid, which upon dehydration gives the common reactive acylium ion reactive species, either Formula 1 or Formula 1a or alternatively a mixture of the same can be combined with Formula 2 in step 1 to generate Formula 3a. In a preferred embodiment, neat methanesulfonic acid is used at 85° C.-95° C., for 1-16 hours. In a further preferred embodiment, between 2-6 volumes of MSA, more preferably between 4 and 5 volumes of MSA, and even more preferably approximately 4.8 volumes of MSA, are used. Alternatively, p-toluenesulfonic acid, benzenesulfonic acid, sulfuric acid or trifluoromethanesulfonic acid, ethanesulfonic acid, acetic acid, propionic acid, trifluoroacetic acid, camphorsulfonic acid, or an acidic solution comprised of one or more of an alkyl sulfonic acid or aryl sulfonic acid with a melting point less than about 250° C., an alky carboxylic acid or aryl carboxylic acid with a melting point less than about 250° C., a non-chloride Brønsted acid, a non-chloride or chloride-immobilized Lewis Acid, or their respective polymer bound or salt preparations, or aqueous solutions thereof, alone or in combination with methanesulfonic acid, may be used to effect cyclization.

The cyclization to Formula 3a can be effected using substantially stoichiometric amounts of reactants (e.g., with a ratio of 2:1 resorcinols of Formula 2 to phthalic anhydrides or di-acids of Formula 1 or Formula 1a). In a further embodiment, it may be preferable to carry out the reaction with an excess of resorcinol (e.g., from about 2.5 equivalents to about 3 or more equivalents, and more preferably about 3.2 or more equivalents) in order to assure complete consumption of phthalic anhydride. After isolation of Formula 3a, the resultant solid can be re-suspended with or without agitation, preferably with heating to 50° C. to 70° C., to improve purity, using water and a combination of acetone and water or DMF and water, and more preferably using acetone and water about 60° C. Isolation and re-suspension may be repeated until the material of Formula 3a is of a desired purity.

The iodination reaction, Step 2 above, may be carried out using molar excess of iodine ($I_2$), preferably under basic conditions. For example, the reaction may be carried out using 0.1-5 M sodium hydroxide, potassium hydroxide, sodium bicarbonate or potassium bicarbonate, at temperatures from 0° C. to reflux. In a preferred embodiment, this reaction may be carried out using 0.4-1.0 M NaOH at 70° C.-95° C. KI, NaI or a mixture of KI and NaI can be used to solubilize iodine in the reaction mixture, for example using NaI at 1-2.5 equivalents. Reaction times range from 1-24 h and are dependent on the number of iodine atoms added to the xanthene ring system.

In a further embodiment, it is possible to control the extent of iodination by varying the reaction time, temperature, or base concentration. Iodine for this reaction may also be generated in situ using an oxidizing agent such as oxone or hydrogen peroxide and iodide salts selected from potassium iodide, lithium iodide, sodium iodide or some mixture thereof. In this particular example, it is preferable to avoid inclusion of components in the reaction mixture that could lead to undesirable transhalogenation, such as aqueous chloride, chlorine, HCl or other components capable of producing halogen ions, unless any oxidizing agent, including atmospheric oxygen and iodine, has been removed or quenched prior to addition of such components. For example sodium hypochlorite is a particularly undesireable component in this reaction mixture since it is a source of labile chloride ions and a potent oxidizer, also chloride ions, chloride radicals, other hypochlorite derivatives, hypochlorous acid and mixtures thereof can lead to the undesireable side reaction. At reaction completion, the mixture can be cooled to approximately −20° C. to 10° C., preferably below 10° C., and iodine can be quenched by addition of an iodine scavenger, such as sodium thiosulfate, potassium thiosulfate, ammonium thiosulfate, potassium sulfite, sodium sulfite or a mixture thereof. In a preferred embodiment, sodium sulfite is used to quench.

Facile isolation of Formula 3 is possible if the pH of the reaction is then adjusted, preferably maintaining a temperature below 10° C. and using neat aqueous sulfuric acid to 1% aqueous solution, preferably 5% sulfuric acid aqueous solution, until the pH is adjusted to between 1.5 and 5, causing Formula 3 to precipitate from solution. In a preferred embodiment, the pH is adjusted to between pH 1.5 and pH 3. After isolation of Formula 3, the resultant solid can be re-suspended and further isolated at ambient temperature to remove impurities, for example using water and a combination of acetone and water or DMF and water, preferably acetone and water. Additionally, pH may be adjusted to 5 or higher to solubilize Formula 3 as Formula 4 prior to conversion back to Formula 3 for isolation under acidic conditions.

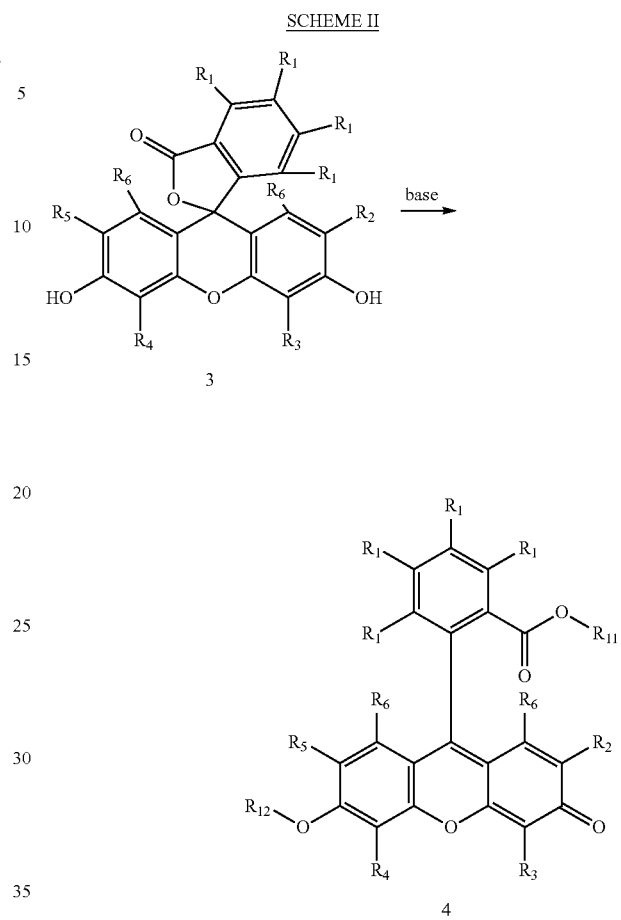

Scheme II shows another embodiment of the present invention, wherein compounds of Formula 3 may also exist in a quinoid form (Formula 4) at substantially neutral or at basic pH, and these quinoids may exist as salts where one or both hydroxyl groups are replaced with a basic counter-ion, $R_{11}$ and/or $R_{12}$, including Na, K or Li ion.

Scheme III shows a method of replacing I with Cl to generate compounds of Formula 3b, where at least one position selected from $R_2, R_3, R_4$ and $R_5$ is Cl, starting from compounds of Formula 3 where at least one position selected from $R_2, R_3, R_4$ and $R_5$ is I.

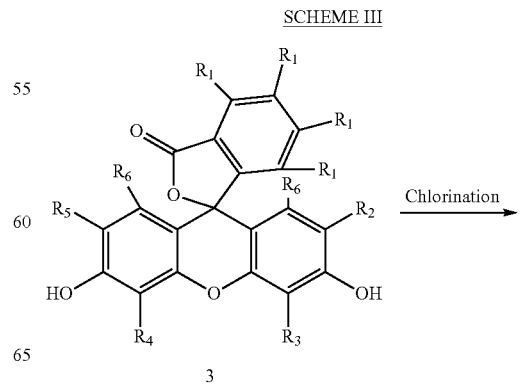

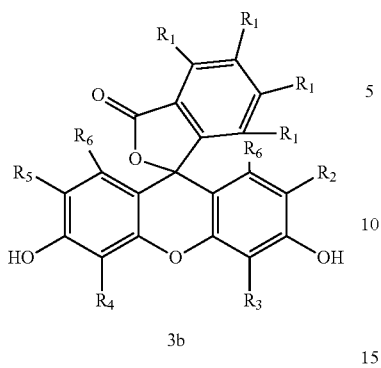

3b

Scheme IV shows another embodiment of the present invention, wherein compounds of Formula 4 may also be isolated as products of this process, and these quinoids may exist as salts where one or both hydroxyl groups at $R_{11}$ and/or $R_{12}$ are replaced with a counter-ion capable of forming a pharmaceutically acceptable salt, including H, Na, K or Li ion.

SCHEME IV

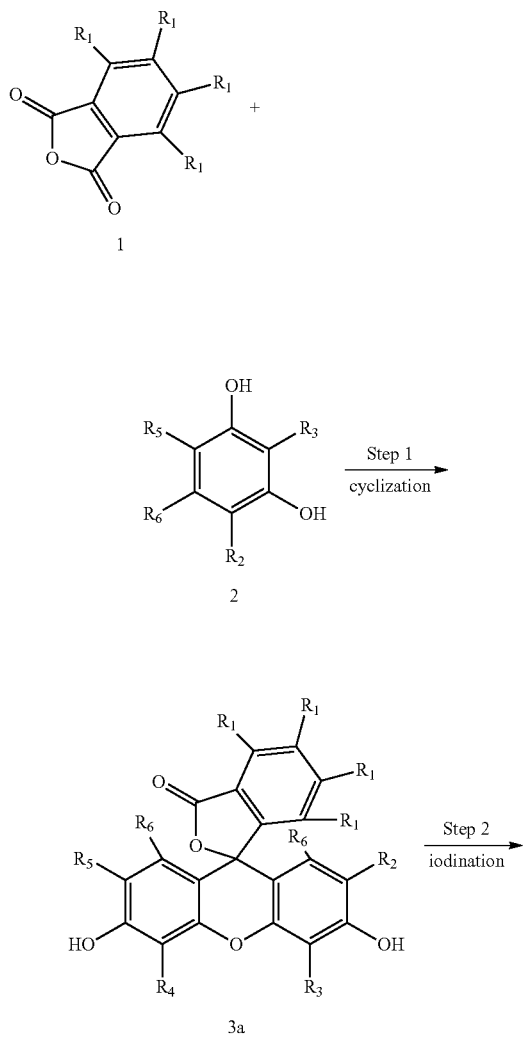

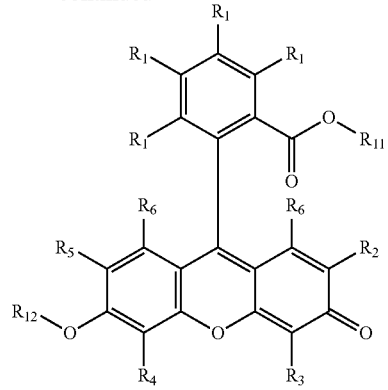

4

Preferred embodiments of the present invention relate to compounds of Formula 3 and Formula 4 where $R_1$ is independently Cl or Br, and $R_2$-$R_5$ are independently selected from Cl, I or H where at least 3 hydrogen atom are present at $R_2$-$R_6$ or at least one chlorine atom is present at $R_2$-$R_5$, and including atropisomers when applicable.

Figure 1K:
FIG. 1k is an illustration of 4,5,6,7-tetrabromo-4'-chloro-3',6'-dihydroxy-2',5',7'-triiodo-3H-spiro[isobenzofuran-1,9'-xanthen]-3-one, also named 4'-chloro-4,5,6,7-tetrabromo-2',5',7'-triiodofluorescein.
Figure 1L:
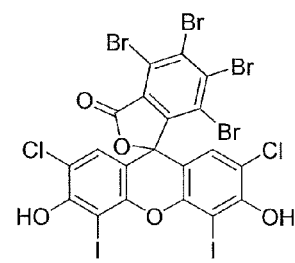
FIG. 1l is an illustration of 4,5,6,7-tetrabromo-2',7'-dichloro-3',6'-dihydroxy-4',5'-diiodo-3H-spiro[isobenzofuran-1,9'-xanthen]-3-one, also named 2',7'-dichloro-4,5,6,7-tetrabromo-4',5'-diiodofluorescein.
Figure 1M:
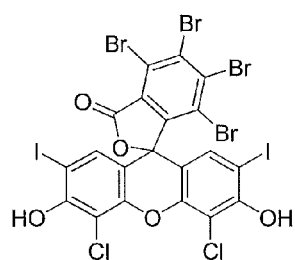
FIG. 1m is an illustration of 4,5,6,7-tetrabromo-4',5'-dichloro-3',6'-dihydroxy-2',7'-diiodo-3H-spiro[isobenzofuran-1,9'-xanthen]-3-one, also named 4',5'-dichloro-4,5,6,7-tetrabromo-2',7'-diiodofluorescein.
Figure 1N:
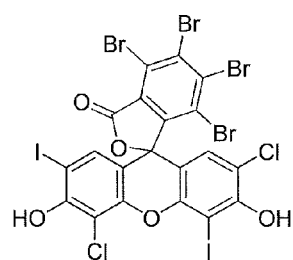
FIG. 1n is an illustration of 4,5,6,7-tetrabromo-2',5'-dichloro-3',6'-dihydroxy-4',7'-diiodo-3H-spiro[isobenzofuran-1,9'-xanthen]-3-one, also named 2',5'-dichloro-4,5,6,7-tetrabromo-4',7'-diiodofluorescein.
Figure 1O:
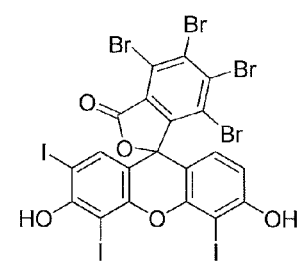
FIG. 1o is an illustration of 4,5,6,7-tetrabromo-3',6'-dihydroxy-2',4',5'-triiodo-3H-spiro[isobenzofuran-1,9'-xanthen]-3-one, also named 4,5,6,7-tetrabromo-2',4',5'-triiodofluorescein.
Figure 1P:
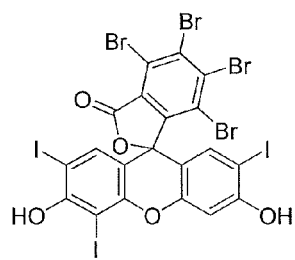
FIG. 1p is an illustration of 4,5,6,7-tetrabromo-3',6'-dihydroxy-2',4',7'-triiodo-3H-spiro[isobenzofuran-1,9'-xanthen]-3-one, also named 4,5,6,7-tetrabromo-2',4',7'-triiodofluorescein.
Figure 1Q:
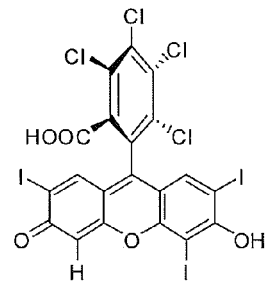
FIG. 1q is an illustration of an atropisomer (aR depiction) of an asymmetrically substituted xanthene.
Figure 1R:
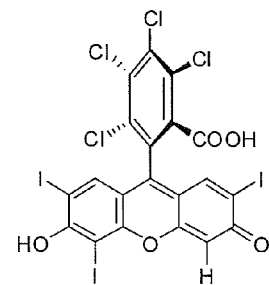
FIG. 1r is an illustration of an atropisomer (aS depiction) of an asymmetrically substituted xanthene.

One set of specific embodiments of the present invention include the following compounds and their pharmaceutically acceptable salts and are named as the lactone form (Formula 3) and the quinoid faun (Formula 4), and are illustrated in FIG. 1:

4,5,6,7-tetrachloro-3',6'-dihydroxy-2',4',5',7'-tetraiodo-3H-spiro[isobenzofuran-1,9'-xanthen]-3-one, also named 4,5,6,7-tetrachloro-2',4',5',7'-tetraiodofluorescein, see FIG. 1a, and its isomeric quinoid form 2,3,4,5-tetrachloro-6-(6-hydroxy-2,4,5,7-tetraiodo-3-oxo-3H-xanthen-9-yl)benzoic acid, see FIG. 1t, commonly referred to as Rose Bengal, or in its disodium salt form as Rose Bengal Disodium;

4,5,6,7-tetrabromo-3',6'-dihydroxy-2',4',5',7'-tetraiodo-3H-spiro[isobenzofuran-1,9'-xanthen]-3-one, also named 4,5,6,7-tetrabromo-2',4',5',7'-tetraiodofluorescein, see FIG. 1b, and its isomeric quinoid form 2,3,4,5-tetrabromo-6-(6-hydroxy-2,4,5,7-tetraiodo-3-oxo-3H-xanthen-9-yl)benzoic acid;

2',4,5,6,7-pentachloro-3',6'-dihydroxy-4',5',7'-triiodo-3H-spiro[isobenzofuran-1,9'-xanthen]-3-one, also named 2',4,5,6,7-pentachloro-4',5',7'-triiodofluorescein, see FIG. 1c, and its isomeric quinoid forms 2,3,4,5-tetrachloro-6-(2-chloro-6-hydroxy-4,5,7-triiodo-3-oxo-3H-xanthen-9-yl)benzoic acid and 2,3,4,5-tetrachloro-6-(7-chloro-6-hydroxy-2,4,5-triiodo-3-oxo-3H-xanthen-9-yl)benzoic acid;

4,4',5,6,7-pentachloro-3',6'-dihydroxy-2',5',7'-triiodo-3H-spiro[isobenzofuran-1,9'-xanthen]-3-one, also named 4,4',5,6,7-pentachloro-2',5',7'-triiodofluorescein, see FIG. 1d, and its isomeric quinoid forms 2,3,4,5-tetrachloro-6-(4-chloro-6-hydroxy-2,5,7-triiodo-3-oxo-3H-xanthen-9-yl)benzoic acid and 2,3,4,5-tetrachloro-6-(5-chloro-6-hydroxy-2,4,7-triiodo-3-oxo-3H-xanthen-9-yl)benzoic acid;

2',4,5,6,7,7'-hexachloro-3',6'-dihydroxy-4',5'-diiodo-3H-spiro[isobenzofuran-1,9'-xanthen]-3-one, also named 2',4,5,6,7,7'-hexachloro-4',5'-diiodofluorescein, see FIG. 1e, and its quinoid form 2,3,4,5-tetrachloro-6-(2,7-dichloro-6-hydroxy-4,5-diiodo-3-oxo-3H-xanthen-9-yl)benzoic acid;

4,4',5,5',6,7-hexachloro-3',6'-dihydroxy-2',7'-diiodo-3H-spiro[isobenzofuran-1,9'-xanthen]-3-one, also named 4,4',5,5',6,7-hexachloro-2',7'-diiodofluorescein, see FIG. 1f, and its quinoid form 2,3,4,5-tetrachloro-6-(4,5-dichloro-6-hydroxy-2,7-diiodo-3-oxo-3H-xanthen-9-yl)benzoic acid;

2',4,5,5',6,7-hexachloro-3',6'-dihydroxy-4',7'-diiodo-3H-spiro[isobenzofuran-1,9'-xanthen]-3-one, also named 2',4,5,5',6,7-hexachloro-4',7'-diiodofluorescein, see FIG. 1g, and its isomeric quinoid focus 2,3,4,5-tetrachloro-6-(2,5-dichloro-6-hydroxy-4,7-diiodo-3-oxo-3H-xanthen-9-yl)benzoic acid and 2,3,4,5-tetrachloro-6-(4,7-dichloro-6-hydroxy-2,5-diiodo-3-oxo-3H-xanthen-9-yl)benzoic acid;

4,5,6,7-tetrachloro-3',6'-dihydroxy-2',4',5'-triiodo-3H-spiro[isobenzofuran-1,9'-xanthen]-3-one, also named 4,5,6,7-tetrachloro-2',4',5'-triiodofluorescein, see FIG. 1h, and its isomeric quinoid forms 2,3,4,5-tetrachloro-6-(6-hydroxy-2,4,5-triiodo-3-oxo-3H-xanthen-9-yl)benzoic acid and 2,3,4,5-tetrachloro-6-(6-hydroxy-4,5,7-triiodo-3-oxo-3H-xanthen-9-yl)benzoic acid;

4,5,6,7-tetrachloro-3',6'-dihydroxy-2',4',7'-triiodo-3H-spiro[isobenzofuran-1,9'-xanthen]-3-one, also named 4,5,6,7-tetrachloro-2',4',7'-triiodofluorescein, see FIG. 1i, and its isomeric quinoid forms 2,3,4,5-tetrachloro-6-(6-hydroxy-2,4,7-triiodo-3-oxo-3H-xanthen-9-yl)benzoic acid and 2,3,4,5-tetrachloro-6-(6-hydroxy-2,5,7-triiodo-3-oxo-3H-xanthen-9-yl)benzoic acid;

4,5,6,7-tetrabromo-2'-chloro-3',6'-dihydroxy-4',5',7'-triiodo-3H-spiro[isobenzofuran-1,9'-xanthen]-3-one, also named 2'-chloro-4,5,6,7-tetrabromo-4',5',7'-triiodofluorescein, see FIG. 1j, and its isomeric quinoid forms 2,3,4,5-tetrabromo-6-(2-chloro-6-hydroxy-4,5,7-triiodo-3-oxo-9,9a-dihydro-3H-xanthen-9-yl)benzoic acid and 2,3,4,5-tetrabromo-6-(7-chloro-6-hydroxy-2,4,5-triiodo-3-oxo-9,9a-dihydro-3H-xanthen-9-yl)benzoic acid;

4,5,6,7-tetrabromo-4'-chloro-3',6'-dihydroxy-2',5',7'-triiodo-3H-spiro[isobenzofuran-1,9'-xanthen]-3-one, also named 4'-chloro-4,5,6,7-tetrabromo-2',5',7'-triiodofluorescein, see FIG. 1k, and its isomeric quinoid focus 2,3,4,5-tetrabromo-6-(4-chloro-6-hydroxy-2,5,7-triiodo-3-oxo-9,9a-dihydro-3H-xanthen-9-yl)benzoic acid and 2,3,4,5-tetrabromo-6-(5-chloro-6-hydroxy-2,4,7-triiodo-3-oxo-9,9a-dihydro-3H-xanthen-9-yl)benzoic acid;

4,5,6,7-tetrabromo-2',7'-dichloro-3',6'-dihydroxy-4',5'-diiodo-3H-spiro[isobenzofuran-1,9'-xanthen]-3-one, also named 2',7'-dichloro-4,5,6,7-tetrabromo-4',5'-diiodofluorescein, see FIG. 1l, and its quinoid form 2,3,4,5-tetrabromo-6-(2,7-dichloro-6-hydroxy-4,5-diiodo-3-oxo-9,9a-dihydro-3H-xanthen-9-yl)benzoic acid;

4,5,6,7-tetrabromo-4',5'-dichloro-3',6'-dihydroxy-2',7'-diiodo-3H-spiro[isobenzofuran-1,9'-xanthen]-3-one, also named 4',5'-dichloro-4,5,6,7-tetrabromo-2',7'-diiodofluorescein, see FIG. 1m, and its quinoid form 2,3,4,5-tetrabromo-6-(4,5-dichloro-6-hydroxy-2,7-diiodo-3-oxo-9,9a-dihydro-3H-xanthen-9-yl)benzoic acid;

4,5,6,7-tetrabromo-2',5'-dichloro-3',6'-dihydroxy-4',7'-diiodo-3H-spiro[isobenzofuran-1,9'-xanthen]-3-one, also named 2',5'-dichloro-4,5,6,7-tetrabromo-4',7'-diiodofluorescein, see FIG. 1n, and its isomeric quinoid forms 2,3,4,5-tetrabromo-6-(2,5-dichloro-6-hydroxy-4,7-diiodo-3-oxo-9,9a-dihydro-3H-xanthen-9-yl)benzoic acid and 2,3,4,5-tetrabromo-6-(4,7-dichloro-6-hydroxy-2,5-diiodo-3-oxo-9,9a-dihydro-3H-xanthen-9-yl)benzoic acid;

4,5,6,7-tetrabromo-3',6'-dihydroxy-2',4',5'-triiodo-3H-spiro[isobenzofuran-1,9'-xanthen]-3-one, also named 4,5,6,7-tetrabromo-2',4',5'-triiodofluorescein, see FIG. 1o, and its isomeric quinoid forms 2,3,4,5-tetrabromo-6-(6-hydroxy-2,4,5-triiodo-3-oxo-3H-xanthen-9-yl)benzoic acid and 2,3,4,5-tetrabromo-6-(6-hydroxy-4,5,7-triiodo-3-oxo-3H-xanthen-9-yl)benzoic acid;

4,5,6,7-tetrabromo-3',6'-dihydroxy-2',4',7'-triiodo-3H-spiro[isobenzofuran-1,9'-xanthen]-3-one, also named 4,5,6,7-tetrabromo-2',4',7'-triiodofluorescein, see FIG. 1p, and its isomeric quinoid forms 2,3,4,5-tetrabromo-6-(6-hydroxy-2,4,7-triiodo-3-oxo-3H-xanthen-9-yl)benzoic acid or isomer 2,3,4,5-tetrabromo-6-(6-hydroxy-2,5,7-triiodo-3-oxo-3H-xanthen-9-yl)benzoic acid;

the aR form, see FIG. 1q, and aS form, see FIG. 1r, of the atropisomers possible whenever one of these compounds is not symmetrically substituted on the xanthene core; and 4,5,6,7-tetrachloro-3',6'-dihydroxy-2',4',5'-triiodo-7'-isopropyl-3H-spiro[isobenzofuran-1,9'-xanthen]-3-one, also named 4,5,6,7-tetrachloro-7'-isopropyl-2',4',5'-triiodofluorescein, see FIG. 1s, and its isomeric quinoid forms 2,3,4,5-tetrachloro-6-(7-isopropyl-6-hydroxy-2,4,5-triiodo-3-oxo-3H-xanthen-9-yl)benzoic acid and 2,3,4,5-tetrachloro-6-(2-isopropyl-6-hydroxy-4,5,7-triiodo-3-oxo-3H-xanthen-9-yl)benzoic acid.

Compounds of Formula 3 or Formula 4 of the present invention may contain chiral centers and therefore may exist in different enantiomeric and diastereomeric forms. The present invention relates to all optical isomers and all stereoisomers of compounds of Formula 3 or Formula 4, both as racemic mixtures and as individual enantiomers, and diastereoisomers of such compounds, and mixtures thereof, and to all pharmaceutical compositions and methods of treatment defined herein that contain or employ them, respectively. Individual isomers can be obtained by known methods, such as optical resolution, fractional crystallization, optically selective reaction conditions or chromatographic separation in the preparation of the final product or its intermediate.

Likewise, the quinoid form of compounds of Formula 3 or Formula 4 where the xanthene ring is not symmetric due to dissimilar substituents on the corresponding xanthene aryl rings (i.e., for example, $R_2 \neq R_5$ when $R_3 = R_4$ or $R_3 \neq R_4$ when $R_2 = R_5$, such as the quinoid forms of compounds depicted in FIGS. 1c, 1d, 1g, 1h, 1i, 1j, 1k, 1o, 1p) may exist as stable atropisomers (as illustrated in FIGS. 1q and 1r). The process described herein encompasses both the minimization of the relative amount of racemic atropisomeric pairs when they may occur as reaction impurities as well as the preparation of these atropisomers as racemic mixtures.

In so far as the compounds of Formula 3 are acidic compounds, they are capable of forming a wide variety of different salts with various inorganic and organic bases. The base addition salts of the acidic compounds of the present invention are readily prepared by treating the lactone of Formula 3 with at least one or two equivalents of the chosen mineral or organic base in an aqueous or suitable organic solvent, such as ethanol or methanol. Upon evaporation of the solvent, filtration or using directly an aqueous solution of the resulting salt, the desired salt is readily obtained in the quinoid form as described by Formula 4. Pharmaceutically acceptable salts include, for example, those formed with sodium, calcium, potassium, magnesium, meglumine, ammonium, aluminum, zinc, piperazine, tromethamin, lithium, choline, diethylamine, 4-phenylcyclohexylamine and benzathine.

The present invention also includes isotopically labeled compounds, which are identical to those of Formula 3 and Formula 4, except that one or more atoms are replaced by an atom having an atomic mass or mass number different from the atomic mass or mass number usually found in nature. Examples of isotopes that can be incorporated into compounds of the present invention include isotopes of hydrogen, carbon, oxygen, fluorine, chlorine and iodine, such as $^2H$, $^3H$, $^{14}C$, $^{13}C$, $^{10}C$, $^{11}C$, $^{13}O$, $^{14}O$, $^{15}O$, $^{18}O$, $^{17}O$, $^{17}F$, $^{18}F$, $^{32}Cl$, $^{33}Cl$, $^{34}Cl$, $^{36}Cl$, $^{74}Br$, $^{75}Br$, $^{76}Br$, $^{77}Br$, $^{117}I$, $^{118}I$, $^{120}I$, $^{121}I$, $^{122}I$, $^{124}I$, $^{126}I$, $^{128}I$ and $^{131}I$, respectively. Compounds of the present invention, prodrugs thereof, and pharmaceutically acceptable salts of said compounds or of said prodrugs which contain the aforementioned isotopes and/or other isotopes of other atoms are within the scope of the present invention. Certain isotopically labeled compounds of the present invention are useful as diagnostic agents in drug/or substrate tissue distribution assays. Isotopically labeled compounds of Formula 3 and Formula 4 and prodrugs thereof can generally be prepared by carrying out the procedures disclosed in the schemes and/or examples below, but substituting a readily available isotopically labeled reagent for a non-isotopically labeled reagent, i.e. $^{131}$I for non-isotopically labeled iodine.

One embodiment of the present invention is where the compound of Formula 4 comprises about 0.001% and less than about 20% by weight in a medicament.

One embodiment of the present invention is directed to medicaments and certain medical uses of such medicaments, and methods for treatment using such medicaments, for treatment of disease of human or animal tissue, wherein a primary active component of such medicaments is a halogenated xanthene of Formula 3 or Formula 4. Such medicaments may function, for example, chemotherapeutically, as chemoablative agents, or as photodynamic agents, and are useful for the treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial, viral, fungal or parasitic infection.

These medicaments are available in various formulations that may include liquid, semisolid, solid or aerosol delivery vehicles, and are suitable for intracorporeal administration via various conventional modes and routes, including intravenous injection (i.v.), intraperitoneal injection (i.p.), intramuscular injection intracranial injection (i.c.), intratumoral injection (i.t.), intralesional injection (i.l.), intraepithelial injection (i.e.), transcutaneous delivery (t.c.), and per oesophageal (p.o.) administration. Additionally, such medicaments are suitable for topical administration via various conventional modes and routes, including topical application directly to or proximal to certain tissues. The active ingredients in such medicaments produce a desirable therapeutic response, such as destruction of microbial infection, reduction or elimination of tissue irritation or inflammation, reduction or elimination of hyperproliferative tissue, reduction or elimination of cancerous or precancerous tissue, reduction or elimination of surface or subsurface lipocytes or lipid deposits, and many other similar indications.

In a preferred embodiment, such medicaments are produced in various formulations including liquid, semisolid, solid or aerosol delivery vehicles, as well as in tablet, capsule, suppository, and other similar forms.

In another preferred embodiment, at least one targeting moiety is coupled to the halogenated xanthene, of Formula 3 or Formula 4, at any of positions $R_1$ to $R_6$ or via attachment at a hydroxyl or carbonyl group. Such targeting moieties may be selected from the group including but not limited to deoxyribonucleic acid (DNA), ribonucleic acid (RNA), amino acids, proteins, antibodies, ligands, haptens, carbohydrate receptors, carbohydrate complexing agents, lipid receptors, lipid complexing agents, protein receptors, protein complexing agents, chelators, encapsulating vehicles, short-chain aliphatic hydrocarbons, long-chain aliphatic hydrocarbons, aromatic hydrocarbons, aldehydes, ketones, alcohols, esters, amides, amines, nitriles, azides, hydrophilic moieties and hydrophobic moieties.

In another preferred embodiment, the compounds of Formula 4 can be used in the manufacture of a medicament.

EXAMPLES

The following examples are intended to be illustrative and non-limiting, and represent specific embodiments of the present invention.

General Methods

All reactions were carried out in open vessels. The vessels were sometimes covered to protect from ambient light. All reactions were carried out under nitrogen, argon or other inert atmosphere unless otherwise noted. All solvents and reagents used were from commercial sources, and no further purification was performed. Reactions were monitored using high-pressure liquid chromatography (HPLC) using either a Agilent 1100 Series Quaternary pump/variable wavelength detector (225 nm detection wavelength) with Supelco Ascentis Express C18 column (4.6×150 mm, 2.7 μm at 40° C., MeCN/0.5% $H_3PO_4$ in $H_2O$, 65/35 to 90/10 gradient running over 30 min) or the same instrument using a Waters Symmetry Shield RP-18 column (4.6×150 mm, 5 μm at 40° C., MeCN/10 mM $K_3PO_4$ pH 3 in $H_2O$+5% MeCN, 10/90 to 80/20 gradient over 25 min or 65/35 isocratic); mass spectrometry (Agilent LC/MSD trap or Waters LCMS with similar chromatography conditions as HPLC, modified with formic acid); and/or thin-layer chromatography (TLC) using UV light and a iodine stain for visualizing. Supercritical fluid chromatography (SFC) was performed using a Thar SFC 80 with a RegisCell column (3×25 cm), loading 20-22 mg/injection at a 4.5 mg/mL concentration in ethanol. Proton nuclear magnetic resonance ($^1$H NMR) spectra were recorded at 300 MHz on a Varian NOVA 300 or Varian Gemini 2000 or at 400 MHz on a Varian Oxford 400, each using TMS as an internal standard. Chemical shifts are reported (as δ units in parts per million, ppm) relative to the singlet at 2.50 ppm for DMSO-$d_6$ referenced to tetramethylsilane (TMS) at 0 ppm. Coupling constants (J) are reported in Hertz (Hz). Noise-decoupled Carbon-13 nuclear magnetic resonance ($^{13}$C NMR) spectra were recorded at 75 MHz on either a Varian NOVA 300, at 100 MHz on a Varian Oxford 400, or at 75 MHz on a Varian Gemini 2000 spectrometer. Chemical shifts are reported as δ in ppm relative to the center line of the septet at 39.5 ppm for DMSO-$d_6$. UV-VIS spectroscopic data were obtained on a Hitachi U-2810 Double Beam Spectrophotometer or on a Spectronic Genesys 2 Spectrophotometer scanning from 200-600 nm, slit width 1.5 nm, path length 10.0 mm Example 1

Preparation of 4,5,6,7-tetrachloro-3',6'-dihydroxy-2', 4',5',7'-tetraiodo-3H-spiro[isobenzofuran-1,9'-xanthen]-3-one (Rose Bengal Lactone, FIG. 1a)

Step 1: Cyclization. A 500 mL round bottom flask was equipped with a heating mantle, J-Kem thermocouple, large magnetic stir bar, nitrogen inlet line, and a magnetic stir plate. This apparatus was charged with tetrachlorophthalic anhydride (1.00 eq, 50.00 g, 174.9 mmol), resorcinol (2.10 eq, 40.44 g, 367.3 mmol), and neat methanesulfonic acid (250 mL). The resulting reaction mixture was a suspension at room temperature. The reaction mixture was purged with nitrogen and heated to 90° C. to give a dark red-orange solution. The reaction was held at 90° C. for 5 hours, and then an additional 5.78 g of resorcinol (0.3 eq, 52.47 mmol) was added. The reaction continued to stir at 90° C. for 2.5 hours. The reaction is deemed to be complete when the amount of residual tetrachlorophthalic anhydride is <1.0% by HPLC. A 1 L round-bottomed flask (3 neck) equipped with a mechanical stirrer, ice bath and J-Kem thermocouple was charged with ambient USP water (500 mL). The 90° C. reaction mixture was added slowly via transfer line to the USP water at <10° C. using a positive pressure of nitrogen. During the transfer of the reaction mixture to water, the transfer rate was controlled such that the temperature of the water quench mixture did not exceed 60° C. An additional 100 mL of USP water was used to rinse the reactor then transferred to the reactor containing the water. The resultant green-brown suspension was allowed to gradually cool to room temperature (RT) and stirred at RT for an additional 30 min. The solids were isolated via vacuum filtration. The reactor was rinsed with USP water (2×250 mL aliquots) and these rinses were used to rinse the wetcake. The wetcake was pulled dry for 60 min, and then dried in vacuo at 70° C. overnight to give 88.60 g of greenish-brown solids. This material, along with 550 mL of acetone was added to a 2 L round bottom flask equipped with a mechanical stirrer, J-Kem thermocouple, heating mantle, nitrogen inlet line, and a Y-adapter with a reflux condenser. The resulting suspension was heated to reflux for 1.5 hours, whereupon it was treated with 530 mL of USP water (slowly added via an addition funnel over 60 min) such that the temperature remained ≥56° C. During the addition of the water, the temperature was observed to rise (maximum temp achieved was 62° C.). After the addition of the water was complete, the yellowish-brown suspension was held at reflux for 3 hours, and then gradually cooled to RT over approximately 30-40 minutes. The mixture was stirred at room temperature for an additional 30 min, and then the yellowish-brown suspension was collected via vacuum filtration. The reactor was rinsed with 50% aqueous acetone (v/v, 4×100 mL), and these rinses were used to rinse the wetcake. The wetcake was allowed to pull dry over 48 h and then further dried in vacuo at 70° C. overnight to give 74.43 g (90.5% yield at 96.8% AUC purity) of tetrachlorofluorescein as a yellow brown solid. $^1$H NMR (300 MHz; DMSO $d_6$) δ 10.23 (S, 2H), 6.95 (d, J=8.7 Hz, 2H), 6.69 (d, J=2.1 Hz, 2H), 6.57 (d of d, J=8.7 Hz, 2H).

Step 2: Iodination. A 500 mL round bottom flask (3-neck) was equipped with a reflux condenser, Y-adapter, J-Kem thermocouple, mechanical stirrer, heating mantle, and a nitrogen inlet line. The reactor was purged with nitrogen and covered with aluminum foil. This was charged with 10.00 grains of tetrachlorofluorescein (21.3 mmol), 30 mL of 5 M NaOH solution and 300 mL of USP water to give a dark red solution. Then, 7.03 grams of sodium iodide (46.9 mmol) and 32.4 g of iodine (127.7 mmol) were charged to the reactor. The reaction mixture was allowed to stir at ambient temperature for 30 min, then it was heated to 90° C. HPLC analysis of an aliquot of the reaction mixture indicated complete consumption of starting material, no partially iodinated intermediates, and complete conversion to the desired product. After the reaction had been heated at 90° C. for 1.5 hours, the heat was turned off, and the reaction mixture was allowed to gradually cool to room temperature over 1.5 hours. The dark purplish-pink reaction mixture was cooled to <10° C. with an ice bath. The pH of the reaction mixture was 7.13. Sodium sulfite (6.70 g) was added to the reaction mixture in small portions. 75 mL of acetone was charged to the reactor at <10° C., and the mixture was allowed to stir for 10 min at <10° C. While at <10° C., 5% aqueous $H_2SO_4$ solution (24 mL) was added dropwise to achieve pH 2.03 and yield a pink suspension. This reaction suspension was collected via vacuum filtration. The reactor was rinsed with 25% aqueous acetone (v/v, 4×100 mL) and the rinses were utilized to rinse the wetcake. The wetcake was pulled dry for 3 hours and dried in vacuo at 60° C. overnight to give 25.81 g of pink solids. These solids and 225 mL of acetone were added to a 1 L round bottom flask (3 neck) equipped with a mechanical stirrer, J-Kem thermocouple, and Y-adapter with nitrogen inlet. This mixture was stirred at room temperature for 10 min, then 255 mL of USP water was added over 10 min to give a suspension. The suspension was stirred at room temperature for 2.25 hours, and then filtered via vacuum filtration to isolate solids. The reactor was rinsed using 50% aqueous acetone (1×75 mL), and this was used to rinse the wetcake. The wetcake was then rinsed with 50% aqueous acetone (2×75 mL) and USP water (1×75 mL), pulled dry for 1 hour and further dried at 80° C. to give 18.68 g of product (90.2% yield, coral pink solids, HPLC AUC purity of 99.5%) of 4,5,6,7-tetrachloro-3',6'-dihydroxy-2',4', 5',7'-tetraiodo-3H-spiro[isobenzofuran-1,9'-xanthen]-3-one.

$^1$H NMR (300 MHz; DMSO $d_6$) δ 10.27 (s, 2H), 7.59 (s, 2H). $^{13}$C NMR (300 MHz; DMSO $d_6$) δ 163.2, 158.6, 151.9, 146.7, 138.8, 136.5, 135.3, 131.2, 126.8, 124.6, 110.8, 81.8, 79.3, 77.0. MS MSD Trap: m/z 974.8 (M+1)$^+$ (exact mass 973.67). UV-VIS λmax=557 nm in methanol; melting point (mp) determined by differential scanning calorimetry (DSC) =215° C.

Example 2

Preparation of 4,5,6,7-tetrabromo-3',6'-dihydroxy-2', 4',5',7'-tetraiodo-3H-spiro[isobenzofuran-1,9'-xanthen]-3-one (FIG. 1b)

Step 1: Treatment of tetrabromophthalic anhydride (28.63 g, 61.74 mmol) and resorcinol (17 g, 154.4 mmol) in 143 mL methanesulfonic acid according to the procedure described in Example 1 Step 1 provided 33.64 g of tetrabromofluorescein was isolated as a light beige solid (84.1% yield, AUC purity of 97.4%). $^1$H NMR (300 MHz; DMSO $d_6$) δ 10.17 (s, 2H), 6.86 (d, J=8.64 Hz, 2H), 6.65 (d, J=2.34 Hz, 2H), 6.54 (d of d, J=8.7 Hz, 2H).

Step 2: Treatment of tetrabromofluorescein (22 g, 33.96 mmol), iodine (51.71 g, 203.7 mmol) and sodium iodide (11.22 g, 74.85 mmol) according to the procedure described in Example 1 Step 2 provided 36.02 g (31.2 mmol, 92.1% yield, AUC purity of 96.3%) of 4,5,6,7-tetrabromo-3',6'-dihydroxy-2',4',5',7'-tetraiodo-3H-spiro[isobenzofuran-1,9'-xanthen]-3-one that was isolated as a light pink solid. $^1$H NMR (300 MHz; DMSO $d_6$) δ 10.22 (s, 2H), 7.49 (s, 2H). $^{13}$C NMR (300 MHz; DMSO $d_6$) δ 163.9, 158.8, 152.5, 149.9, 137.3, 136.7, 133.5, 127.5, 124.6, 121.1, 111.5, 82.0, 80.3, 77.4. MS MSD Trap: m/z 1152.6 (M+1)$^+$ (exact mass 1151.48). UV-VIS λmax=558 nm in methanol, mp (determined by DSC)=227° C.

Example 3

Preparation of 2',4,5,6,7-pentachloro-3',6'-dihydroxy-4',5',7'-triiodo-3H-spiro[isobenzofuran-1,9'-xanthen]-3-one (FIG. 1c)

Step 1: Treatment of tetrachlorophthalic anhydride (5 g, 17.48 mmol), 4-chlororesorcinol (2.78 g, 19.23 mmol) and resorcinol (2.12 g, 19.23 mmol) according to the procedure described in Example 1 Step 1 provided 7.24 g of 18.6% pure 2',4,5,6,7-pentachloro-3',6'-dihydroxy-3H-spiro[isobenzofuran-1,9'-xanthen]-3-one that was collected and taken to the next step as a mixture.

Step 2: 2',4,5,6,7-pentachloro-3',6'-dihydroxy-3H-spiro[isobenzofuran-1,9'-xanthen]-3-one (7.24 g, 15.4 mmol) was iodinated according to the procedure described in Example 1, Step 2. Crude product (5.47 g) was then isolated via SFC purification (80 g/min total flow, 40% co-solvent (EtOH/0.5% TFA) in $CO_2$, 140 bar, 254 nm on a 3×25 cm 5 m RegisPack column) to give 427 mg (0.54 mmol, 34.7% yield) of 2',4,5,6,7-pentachloro-3',6'-dihydroxy-4',5',7'-triiodo-3H-spiro[isobenzofuran-1,9'-xanthen]-3-one, a light pink solid in 95.8% AUC HPLC purity. $^1$H NMR (300 MHz; DMSO $d_6$) δ 10.85 (s, 1H), 10.2 (s, 1H), 7.60 (s, 1H), 7.38 (s, 1H). $^{13}$C NMR (300 MHz; DMSO $d_6$) δ 163.4, 159.0, 155.8, 152.3, 151.2, 146.9, 139.1, 136.9, 135.7, 131.6, 128.2, 127.1, 125.1, 116.9, 111.0, 109.7, 82.3, 80.0, 78.4, 78.4, 77.5. MS MSD Trap: m/z 882.7 $(M+1)^+$ (exact mass 882.2). UV-VIS λmax=554 nm in methanol.

Example 4

Degradation of 4,5,6,7-tetrachloro-3',6'-dihydroxy-2',4',5',7'-tetraiodo-3H-spiro[isobenzofuran-1,9'-xanthen]-3-one to 4,4',5,6,7-pentachloro-3',6'-dihydroxy-2',5',7'-triiodo-3H-spiro[isobenzofuran-1,9'-xanthen]-3-one and 4,4',5,5',6,7-hexachloro-3',6'-dihydroxy-2',7'-diiodo-3H-spiro[isobenzofuran-1,9'-xanthen]-3-one (FIGS. 1a, 1d and 1f)

To 100 mg (0.10 mmol), of 4,5,6,7-tetrachloro-3',6'-dihydroxy-2',4',5',7'-tetraiodo-3H-spiro[isobenzofuran-1,9'-xanthen]-3-one was added 1.0 mL of acetonitrile and 2.0 mL of 12.5% aqueous sodium hypochlorite at room temperature. The reaction mixture was allowed to stir at RT for 1 hour. HPLC analysis indicated two new impurities at 8.38 min and 9.93 min retention time (27.8% and 45.6%, respectively), with 26.6% of 4,5,6,7-tetrachloro-3',6'-dihydroxy-2',4',5',7'-tetraiodo-3H-spiro[isobenzofuran-1,9'-xanthen]-3-one remaining unreacted. Mass spectral analysis showed M-1 ions: M-1=791.7 corresponding to a hexachloro impurity, M-1=881.4 corresponding to a pentachloro impurity, and M-1=973.2 corresponding to Rose Bengal lactone. The transhalogenated compounds were made individually below (see examples 5 and 7), to confirm the structural assignments and correlated to the products of this example using HPLC.

Example 5

Preparation of 4,4',5,6,7-pentachloro-3',6'-dihydroxy-2',5',7'-triiodo-3H-spiro[isobenzofuran-1,9'-xanthen]-3-one (FIG. 1d)

Step 1: Tetrachlorophthalic anhydride (2.5 g, 8.74 mmol), 2-chlororesorcinol (1.33 g, 9.18 mmol) and resorcinol (1.01 g, 9.18 mmol) were combined with 12.5 mL of neat methanesulfonic acid and heated to 90° C. for 19 h then to 97° C. for 10 h whereupon the hot mixture was carefully added to 25 mL of ice water. This suspension was extracted into ethyl acetate and washed with water and brine, then dried over sodium sulfate. The product was isolated via a silica gel plug using 66%:14%:18%:4% toluene:dioxane:hexane:acetic acid as the eluent. 1.95 g of 46.4% pure 4,4',5,6,7-pentachloro-3',6'-dihydroxy-3H-spiro[isobenzofuran-1,9'-xanthen]-3-one was collected and taken to the next step without further purification.

Step 2: 4,4',5,6,7-pentachloro-3',6'-dihydroxy-3H-spiro[isobenzofuran-1,9'-xanthen]-3-one (1.95 g, 4.15 mmol) was iodinated according to the procedure described in Example 1, Step 2. Crude yield, 2.70 g of a mixture. Product was isolated via SFC purification (80 g/min total flow, 40% co-solvent IPA in $CO_2$, 140 bar, 254 nm on a 3×25 cm 5 m RegisPack column) to give 630 mg (0.7 mmol, 38.5% yield, 98.7% AUC purity) of 4,4',5,6,7-pentachloro-3',6'-dihydroxy-2',5',7'-triiodo-3H-spiro[isobenzofuran-1,9'-xanthen]-3-one as a pink solid. $^1$H NMR (300 MHz; DMSO $d_6$) δ 11.05 (s, 1H), 10.3 (s, 1H), 8.3 (s, 1H), 7.55 (d, 2H). $^{13}$C NMR (300 MHz; DMSO $d_6$) δ 163.2, 158.6, 154.7, 150.7, 148.0, 146.7, 138.7, 136.5, 135.3, 134.5, 131.3, 126.8, 124.6, 110.5, 110.4, 82.4, 82.1, 79.3, 77.6. MS MSD Trap: m/z 882.7 $(M+1)^+$ (exact mass 882.2). UV-VIS λmax=555 nm in methanol Example 6

Preparation of 2',4,5,6,7,7'-hexachloro-3',6'-dihydroxy-4',5'-diiodo-3H-spiro[isobenzofuran-1,9'-xanthen]-3-one (FIG. 1e)

Step 1: Treatment of tetrachlorophthalic anhydride (5 g, 17.49 mmol) and 4-chlororesorcinol (6.32 g, 43.73 mmol), according to the procedure described in Example 1 Step 1, provided 10.31 g of crude product. Suspension of a 9.25 g portion of this in DMF:water (1:1) followed by filtration, provided 9.70 g (2:1 DMF complex 17.16 mmol, 92.3% yield) of 2',4,5,6,7,7'-hexachloro-3',6'-dihydroxy-3H-spiro[isobenzofuran-1,9'-xanthen]-3-one that was isolated as an orange solid. $^1$H NMR (300 MHz; DMSO $d_6$) δ 11.13 (S, 2H), 7.31 (s, 2H), 6.89 (s, 2H).

Step 2: Treatment of 2',4,5,6,7,7'-hexachloro-3',6'-dihydroxy-3H-spiro[isobenzofuran-1,9'-xanthen]-3-one (2 g, 3.71 mmol) according to the procedure described in Example 1, Step 2 provided 2.56 g (3.22 mmol, 87.3% yield) of 2',4,5,6,7,7'-hexachloro-3',6'-dihydroxy-4',5'-diiodo-3H-spiro[isobenzofuran-1,9'-xanthen]-3-one that was isolated as a pink-orange solid in 97.9% AUC HPLC purity. $^1$H NMR (300 MHz; DMSO $d_6$) δ 10.90 (s, 2H), 7.48 (s, 2H). $^{13}$C NMR (300 MHz; DMSO $d_6$) δ 163.2, 154.7, 147.1, 146.8, 138.7, 135.3, 134.5, 131.3, 126.7, 124.5, 110.3, 107.7, 82.6, 79.0. MS MSD Trap: m/z 791.0 $(M+1)^+$ (exact mass 790.77). UV-VIS λmax=551 nm in methanol.

Example 7

Preparation of 4,4',5,5',6,7-hexachloro-3',6'-dihydroxy-2',7'-diiodo-3H-spiro[isobenzofuran-1,9'-xanthen]-3-one (FIG. 1f)

Step 1: Treatment of tetrachlorophthalic anhydride (5 g, 17.49 mmol) and 2-chlororesorcinol (7.58 g, 41.98 mmol) according to the procedure described in Example 1, Step 1, provided 9.3 g of the crude product. Suspension of 8 g of the crude 9.3 g in DMF:water (1:1), followed by filtration provided 8.65 g (16.05 mmol, 91.7% AUC yield) of 4,4',5,5',6,7-hexachloro-3',6'-dihydroxy-3H-spiro[isobenzofuran-1,9'-xanthen]-3-one that was isolated as an orange solid. $^1$H NMR (300 MHz; DMSO $d_6$) δ 11.09 (S, 2H), 7.03 (d, J=9 Hz, 2H), 6.81 (d, J=8.7 Hz, 2H).

Step 2: Treatment of 4,4',5,5',6,7-hexachloro-3',6'-dihydroxy-3H-spiro[isobenzofuran-1,9'-xanthen]-3-one (2 g, 3.71 mmol) according to the procedure described in Example 1, Step 2 provided 2.20 g (2.78 mmol, 75.1% yield) of 4,4',5,5',6,7-hexachloro-3',6'-dihydroxy-2',7'-diiodo-3H-spiro[isobenzofuran-1,9'-xanthen]-3-one that was isolated as a pink-orange solid at 97.7% AUC HPLC purity. $^1$H NMR (300 MHz; DMSO $d_6$) δ 11.05 (s, 2H), 7.58 (s, 2H). $^{13}$C NMR (300 MHz; DMSO $d_6$) δ 163.2, 154.7, 147.1, 146.8, 138.7, 135.3, 134.5, 131.3, 126.7, 124.5, 110.3, 107.7, 82.8, 79.0. MS MSD Trap: m/z 791.0 $(M+1)^+$ (exact mass 790.77). UV-VIS λmax=554 nm in methanol.

Example 8

Preparation of 2',4,5,5',6,7-hexachloro-3',6'-dihydroxy-4',7'-diiodo-3H-spiro[isobenzofuran-1,9'-xanthen]-3-one (FIG. 1g)

Step 1: Treatment of tetrachlorophthalic anhydride (5 g, 17.48 mmol), 4-chlororesorcinol (2.78 g, 19.23 mmol) and 2-chlororesorcinol (2.78 g, 19.23 mmol) according to the procedure described in Example 1, Step 1 provided 6.2 g of crude product (approximately 54% pure by HPLC 2',4,5,5', 6,7-hexachloro-3',6'-dihydroxy-3H-spiro[isobenzofuran-1, 9'-xanthen]-3-one) that was collected and taken to the next step as a mixture.

Step 2: 2',4,5,5',6,7-pentachloro-3',6'-dihydroxy-3H-spiro [isobenzofuran-1,9'-xanthen]-3-one (6.2 g, 54.4% desired compound, 6.25 mmol) was iodinated according to the procedure described in Example 1, Step 2, yielding 7.16 g (60.8% desired compound, 5.50 mmol, 88% yield). Crude product (3.37 g, 60.8% desired compound, 2.59 mmol) was isolated via SFC purification (80 g/min total flow, 40% co-solvent (50/50 IPA/EtOH 0.5% TFA in $CO_2$, 140 bar, 254 nm on a 3×25 cm 5 m RegisPack column) to give 427 mg (0.54 mmol, 20.8% recovery from SFC) of 2',4,5,5',6,7-hexachloro-3',6'-dihydroxy-4',7'-diiodo-3H-spiro[isobenzofuran-1,9'-xanthen]-3-one as a light pink solid. $^1$H NMR (300 MHz; DMSO $d_6$) δ 11.05 (s, 1H), 10.85 (s, 1H), 7.60 (s, 1H), 7.40 (s, 1H). $^{13}$C NMR (300 MHz; DMSO $d_6$) δ 163.1, 155.4, 154.7, 149.6, 148.0, 146.5, 138.7, 135.3, 134.5, 131.3, 127.9, 126.8, 124.7, 116.7, 110.3, 109.0, 107.5, 82.4, 79.6, 78.5. MS MSD Trap: m/z 790.7 $(M+1)^+$ (exact mass 790.7). UV-VIS λmax=552 nm in methanol.

Example 9

Degradation of 4,5,6,7-tetrachloro-3',6'-dihydroxy-2', 4',5',7'-tetraiodo-3H-spiro[isobenzofuran-1,9'-xanthen]-3-one to 4,5,6,7-tetrachloro-3',6'-dihydroxy-2', 4',7'-triiodo-3H-spiro[isobenzofuran-1,9'-xanthen]-3-one (FIGS. 1a and 1i)

To 6.5 g (6.67 mmol) of 4,5,6,7-tetrachloro-3',6'-dihydroxy-2',4',5',7'-tetraiodo-3H-spiro[isobenzofuran-1,9'-xanthen]-3-one was added 130 mL acetone, 30 mL of water and 6.6 g sodium iodide (44.0 mmol). The mixture was heated to reflux for 82.5 h and HPLC analysis indicated 35.4% of the title compound was present in a mixture with starting material. The reaction mixture was diluted with 130 mL of water and 150 mL of ethyl acetate and allowed to stand overnight at room temperature. The organic layer was removed, and the aqueous layer was extracted with 100 mL ethyl acetate. The combined organic layers were washed with brine and dried over sodium sulfate, yielding 6.73 g crude product containing 35.4% of the title compound by HPLC. The title compound was isolated via silica gel chromatography from a portion of this material using 66%:14%:18%:4% toluene: dioxane:hexane:acetic acid. After successive chromatography steps, 4,5, 6,7-tetrachloro-3',6'-dihydroxy-2',4',7'-triiodo-3H-spiro [isobenzofuran-1,9'-xanthen]-3-one was isolated as a red solid (90 mg). $^1$H NMR (300 MHz; DMSO $d_6$) δ 11.26, (s, 1H), 10.19 (s, 1H), 7.56 (s, 1H), 7.51 (s, 1H), 6.84 (s, 1H). $^{13}$C NMR (300 MHz; DMSO $d_6$) δ 163.4, 159.0, 158.3, 151.8, 150.8, 147.2, 138.6, 136.9, 135.1, 126.7, 124.5, 110.6, 108.8, 101.7, 81.2, 88.7, 77.1. MS MSD Trap: m/z 848.8 $(M+1)^+$ (exact mass 847.7). UV-VIS λmax=539 nm in methanol.

Example 10

Preparation of 4,5,6,7-tetrachloro-2',4',5'-triiodofluorescein (FIG. 1h) and related compounds by incomplete iodination A 500 mL round bottom flask was charged with 10 g (21.3 mmol) tetrachlorofluorescein, 13 mL 5 M NaOH, 300 mL water, 7.08 g NaI (47.2 mmol) and 16.24 g iodine (64 mmol). The solution was heated to 50° C. for 6.5 h before it was cooled to room temperature. Sodium hydrogen sulfite was added followed by acetic acid until the pH was 3.7. The mixture was extracted with ethyl acetate, washed with water then brine and dried over sodium sulfate, filtered and concentrated in vacuo. 18.2 g of a reddish-orange foam was isolated as a mixture of 46% 4,5,6,7-tetrachloro-4',5'-diiodofluorescein and 43% of the title compound, 4,5,6,7-tetrachloro-2',4', 5'-triiodofluorescein by AUC HPLC purity. LCMS MS Scan 800-1000: m/z 846.52 $(M-1)^-$ (exact mass 847.7). UV-VIS λmax=540 nm in PBS. In comparison to example 1 where 6 equivalents of iodine at 90° C. yields substantially quantitative conversion to the tetraiodinated product, this reaction using milder heating and 3 equivalents of iodine yields a mixture of lower iodinated impurities. This demonstrates the utility of varying reaction conditions to control the yield of lower iodinated products.

Example 11

Degradation of 4,5,6,7-tetrachloro-3',6'-dihydroxy-2', 4',5',7'-tetraiodo-3H-spiro[isobenzofuran-1,9'-xanthen]-3-one to 4,5,6,7-tetrachloro-3',6'-dihydroxy-2', 4',5'-triiodo-7'-isopropyl-3H-spiro[isobenzofuran-1, 9'-xanthen]-3-one (FIGS. 1a and 1s)

To a round bottom flask charged with $ZnCl_2$ (0.5 mL, 0.50 mmol), isopropylmagnesium chloride (0.23 mL, 0.45 mmol), and $Bis(PPh_3)_2PdCl_2$ (catalytic amount) in THF at room temperature, 200 mg (0.21 mmol) 4,5,6,7-tetrachloro-3',6'-dihydroxy-2',4',5',7'-tetraiodo-3H-spiro[isobenzofuran-1,9'-xanthen]-3-one in 2 mL THF was added. The solution was stirred at room temperature for 38 h. The reaction was quenched with 5 mL of USP water, 0.5 mL acetic acid and 2 drops of 5M sulfuric acid. The organic layer was washed with USP water (3 mL), dried over sodium sulfate and concentrated in vacuo. 195 mg of an orange-red solid was isolated as a mixture of 2.3% of the title compound and 42.9% of 4,5,6,7-tetrachloro-3',6'-dihydroxy-2',4',5',7'-tetraiodo-3H-spiro[isobenzofuran-1,9'-xanthen]-3-one by HPLC. To confirm the structure, an isolation of the title compound was undertaken in the following example.

Example 12

Isolation of 4,5,6,7-tetrachloro-3',6'-dihydroxy-2',4', 5'-triiodo-7'-isopropyl-3H-spiro[isobenzofuran-1,9'-xanthen]-3-one from 2,3,4,5-tetrachloro-6-(6-hydroxy-2,4,5,7-tetraiodo-3-oxo-3H-xanthen-9-yl) benzoic acid disodium salt (FIGS. 1s from 1t)

118 g (0.11 mol) of commercial grade Rose Bengal disodium salt was dissolved in 985 mL of USP water and acidified to pH 1-2 with 400 mL of 1 M HCl to give a slurry. The slurry was extracted with 1800 mL of ethyl acetate and the organic layer separated. The aqueous layer was extracted with an additional 100 mL of ethyl acetate and the organic layer separated. The combined organic layers were concentrated until about 1800 mL of solvent remained. The slurry was then treated with 500 mL of heptane, filtered and the wetcake rinsed with 250 mL of heptane. The solids were dried at 60° C. and then combined with 760 mL of dioxane in a foil-covered flask under nitrogen atmosphere. The resulting slurry was heated to 95° C. and held at temperature for 70 min. The slurry was cooled and filtered. Under nitrogen, the wet cake was rinsed with 2 volumes of dioxane and dried. This sample was dissolved in 45 mL of THF (inhibitor-free), concentrated to 15-20 mL and loaded onto an alumina column (510 g neutral alumina with 300 mL of a 90 Acetonitrile: 10 Isopropanol:1 Acetic Acid:1 $H_2O$ solution). The column was eluted using the same solution and the fractions containing product were combined, concentrated under reduced pressure and axeotropically dried from heptane. This procedure was repeated a second time before the resultant isolated solids were dissolved in anhydrous THF and loaded onto a silica gel prep plate. The prep plate was eluted once using 66% toulene: 14% dioxane: 18% heptane: 4% acetic acid. The upper band was scraped off the prep plate and digested with 10 mL of anhydrous THF, filtered and rinsed with 20 mL of THF. The filtrate was concentrated in vacuo to afford 59 mg of title compound as an orange red residue in 85% AUC HPLC purity. $^1$H NMR (300 MHz; Acetone $d_6$) δ 7.67 (s, 1H), 6.99 (s, 1H), 3.27 (m, 1H), 1.12 (d, J=5.4 Hz 3H), 1.06 (d, J=5.1 Hz, 3H). MS MSD Trap: m/z 888.6 (M−1)$^-$ (exact mass 887.65). UV-VIS λmax=552 nm in methanol.

This description has been offered for illustrative purposes only and is not intended to limit the invention of this application.

What is claimed as new and desired to be protected by Letters Patent is set forth in the appended claims.

We claim:
1. A process for the preparation of a compound of Formula 4:

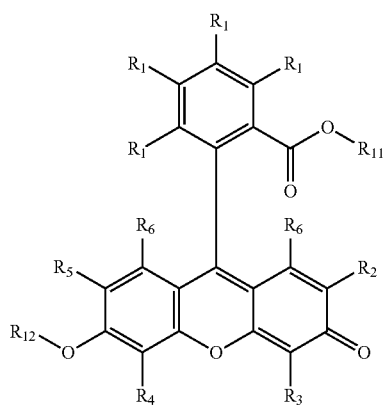

wherein $R_1$ is independently Cl or Br, $R_2$, $R_3$, $R_4$ and $R_5$ are I, $R_6$ is H, and $R_{11}$ and $R_{12}$ are independently H or a counter-ion capable of forming a pharmaceutically acceptable salt, comprising:

a) combining a compound of Formula 1a,

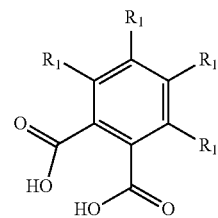

wherein $R_1$ is independently Cl or Br, with about two equivalents of a compound of Formula 2,

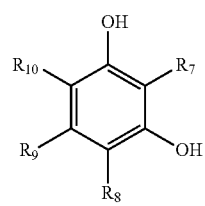

wherein $R_7$, $R_8$, $R_9$ and $R_{10}$ are H, in an acidic solution substantially free of chloride ions and substantially free of chloride-ion producing impurities, to form an intermediate compound of Formula 3a,

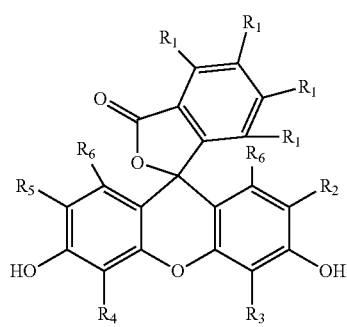

wherein $R_1$ is independently Cl or Br and $R_2$, $R_3$, $R_4$, $R_5$ and $R_6$ are H;

b) combining the intermediate compound of Formula 3a with at least 4 equivalents of iodine in a solution substantially free of chloride ions and substantially free of chloride-producing impurities to form the compound of Formula 4 substantially free of transhalogenated impurities of the compound of Formula 4 wherein $R_1$ is independently Cl or Br; at least one of $R_2$, $R_3$, $R_4$ and $R_5$ is Cl and the remainder are I; $R_6$ is H; and $R_{11}$ and $R_{12}$ are independently H, Na, K, Li, or a counter-ion capable of forming a pharmaceutically acceptable salt.

2. The process of claim 1 wherein a transhalogenated impurity of the compound of Formula 4 comprises less than 0.15 percent by weight.

3. The process of claim 1 wherein the transhalogenated impurities comprise at least one compound selected from the group consisting of:
2',4,5,6,7-pentachloro-3',6'-dihydroxy-4',5',7'-triiodo-3H-spiro[isobenzofuran-1,9'-xanthen]-3-one; 4,4',5,6,7- pentachloro-3',6'-dihydroxy-2',5',7'-triiodo-3H-spiro[isobenzofuran-1,9'-xanthen]-3-one; 2',4,5,6,7,7'-hexachloro-3',6'-dihydroxy-4',5'-diiodo-3H-spiro[isobenzofuran-1,9'-xanthen]-3-one; 4,4',5,5',6,7-hexachloro-3',6'-dihydroxy-2',7'-diiodo-3H-spiro[isobenzofuran-1,9'-xanthen]-3-one; 2',4,5,5',6,7-hexachloro-3',6'-dihydroxy-4',7'-diiodo-3H-Spiro[isobenzofuran-1,9'-xanthen]-3-one;

an isomeric quinoid thereof; and mixtures thereof.

4. The process of claim 1 wherein the acidic solution comprises less than 1500 ppm chloride.

5. The process of claim 1 wherein the acidic solution comprises at least one acid selected from the group consisting of an alkyl sulfonic acid or aryl sulfonic acid with a melting point of less than 250° C., an alkyl carboxylic acid or aryl carboxylic acid with a melting point of less than 250° C., a non-chloride Brønsted acid, a non-chloride Lewis Acid, a polymer bound preparation thereof, a salt thereof, an aqueous solution thereof, and mixtures thereof, alone or in combination with methanesulfonic acid.

6. The process of claim 1 wherein the acidic solution comprises at least one acid selected from the group consisting of p-toluenesulfonic acid, benzenesulfonic acid, sulfuric acid, trifluoromethanesulfonic acid, ethanesulfonic acid, acetic acid, propionic acid, trifluoroacetic acid, camphorsulfonic acid, a polymer bound preparation thereof, a salt thereof, an aqueous solution thereof, and mixtures thereof, alone or in combination with methanesulfonic acid.

7. The process of claim 1 wherein the acidic solution comprises methanesulfonic acid.

8. The process of claim 1 wherein the compounds of Formula 2 and Formula 1a are combined in a ratio in the range of 2.5:1 to 3.2:1.

9. The process of claim 1 further comprising heating the compounds of Formula 1a and Formula 2 in the acidic solution at a temperature in the range of 85° C. to 95° C. for a time period of 1 to 16 hours.

10. The process of claim 1 wherein the compound of Formula 1a is in a mixture with Formula 1

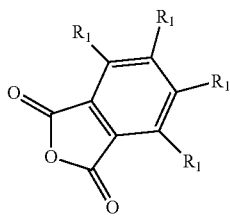

and the mixture is combined with two equivalents of the compound of Formula 2.

11. The process of claim 1 further comprising isolating the intermediate compound of Formula 3a.

12. The process of claim 11 wherein the isolating comprises suspension of the intermediate compound of Formula 3a, collection of the intermediate compound of Formula 3a, and rinsing the intermediate compound of Formula 3a with a substantially chloride-ion-free solvent.

13. The process of claim 12 wherein the solvent comprises a mixture of acetone and water heated to 60° C.

14. The process of claim 1 wherein the solution containing the intermediate compound of Formula 3a and iodine comprises less than 1500 ppm chloride.

15. The process of claim 1 further comprising heating the combined intermediate compound of Formula 3a and iodine in basic solution at a temperature in the range of 20° C. to 100° C. for a time period in the range of 1 to 24 hours.

16. The process of claim 15 further comprising heating the combined intermediate compound of Formula 3a and iodine in solution at a temperature in the range of 70° C. to 95° C. for a time period in the range of 1 to 24 hours.

17. The process of claim 1 wherein the solution comprises at least one base selected from the group consisting of sodium hydroxide, potassium hydroxide, lithium hydroxide, sodium bicarbonate, potassium bicarbonate, and mixtures thereof.

18. The process of claim 1 wherein the solution comprises sodium hydroxide at a concentration of 0.4 to 1.0 M.

19. The process of claim 1 further comprising adding at least one iodine-solubilizing agent to the solution comprising the intermediate compound of Formula 3a and iodine wherein the iodine-solubilizing agent is selected from the group consisting of potassium iodide, lithium iodide, sodium iodide, and mixtures thereof.

20. The process of claim 19 wherein the iodine-solubilizing agent comprises 1 to 2.5 equivalents of sodium iodide.

21. The process of claim 1 wherein iodine is generated in situ by adding to the solution an oxidizing agent and an iodide salt wherein the solution is substantially free of chloride ions, chloride-ion free radicals, hypochlorite, hypochlorous acid or mixtures thereof.

22. The process of claim 1 further comprising adding an iodine scavenger to the solution subsequent to the formation of the compound of Formula 4, wherein the scavenger is selected from the group consisting of sodium thiosulfate, potassium thiosulfate, ammonium thiosulfate, potassium sulfite, sodium sulfite and mixtures thereof.

23. The process of claim 22 wherein the iodine scavenger is sodium sulfite.

24. The process of claim 23 wherein the addition of the iodine scavenger is performed at a temperature of 10° C. or lower.

25. The process of claim 1 wherein $R_{11}$ and $R_{12}$ are sodium.

26. A process for the preparation of a compound of Formula 3

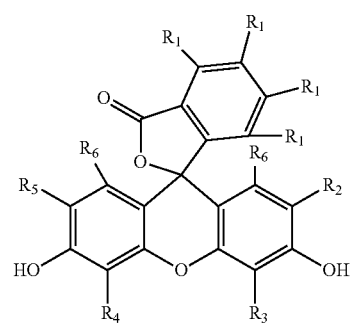

wherein $R_1$ is independently Cl or Br, $R_2$, $R_3$, $R_4$ and $R_5$ are I and $R_6$ is H, comprising:
a) combining a compound of Formula 1a,

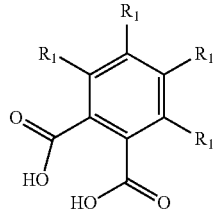

wherein $R_1$ is independently Cl or Br, with two equivalents of a compound of Formula 2,

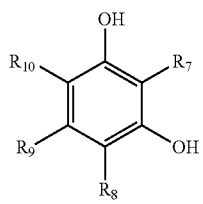

wherein $R_7$, $R_8$, $R_9$ and $R_{10}$ are H, in an acidic solution at a temperature in the range of 20° C. to 250° C. to form a compound of Formula 3a;
b) isolating the intermediate compound of Formula 3a,

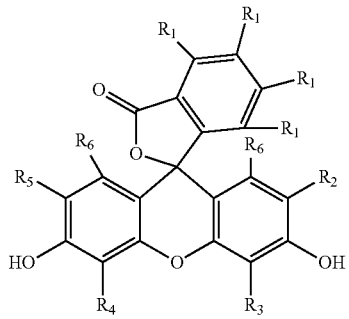

wherein $R_1$ is independently Cl or Br and $R_2$, $R_3$, $R_4$, $R_5$ and $R_6$ are H;
c) combining the intermediate compound of Formula 3a with 4 equivalents of iodine in a solution substantially free of chloride ions and substantially free of chloride-ion-producing impurities at a temperature in the range of 20° C. to 100° C. to form the compound of Formula 3;
d) adding an iodine scavenger to the compound of Formula 3;
e) acidifying the compound of Formula 3 to a pH of less than 5 and cooling to a temperature of less than 10° C.; and
f) isolating the compound of Formula 3 substantially free of transhalogenated impurities wherein $R_1$ is independently Cl or Br, at least one of $R_2$, $R_3$, $R_4$ and $R_5$ is Cl and the remainder are I, and $R_6$ is H.

27. The process of claim 26 wherein a transhalogenated impurity of the compound of Formula 3 comprises less than 0.15 percent by weight.

28. The process of claim 26 wherein the transhalogenated impurities comprise at least one compound selected from the group consisting of:
2',4,5,6,7-pentachloro-3',6'-dihydroxy-4',5',7'-triiodo-3H-spiro[isobenzofuran-1,9'-xanthen]-3-one; 4,4',5,6,7-pentachloro-3',6'-dihydroxy-2',5',7'-triiodo-3H-spiro[isobenzofuran-1,9'-xanthen]-3-one; 2',4,5,6,7,7'-hexachloro-3',6'-dihydroxy-4',5'-diiodo-3H-spiro[isobenzofuran-1,9'-xanthen]-3-one; 4,4',5,5',6,7-hexachloro-3',6'-dihydroxy-2',7'-diiodo-3H-spiro[isobenzofuran-1,9'-xanthen]-3-one; 2',4,5,5',6,7-hexachloro-3',6'-dihydroxy-4',7'-diiodo-3H-spiro[isobenzofuran-1,9'-xanthen]-3-one;
an isomeric quinoid thereof; and mixtures thereof.

29. The process of claim 26 wherein the acidic solution comprises less than 1500 ppm chloride.

30. The process of claim 26 wherein the acidic solution comprises at least one acid selected from the group consisting of an alkyl sulfonic acid or aryl sulfonic acid with a melting point of less than 250° C., an alkyl carboxylic acid or aryl carboxylic acid with a melting point of less than 250° C., a non-chloride Brønsted acid, a non-chloride Lewis Acid, a polymer bound preparation thereof, a salt thereof, an aqueous solution thereof, and mixtures thereof, alone or in combination with methanesulfonic acid.

31. The process of claim 26 wherein the acidic solution comprises at least one acid selected from the group consisting of p-toluenesulfonic acid, benzenesulfonic acid, sulfuric acid, trifluoromethanesulfonic acid, ethanesulfonic acid, acetic acid, propionic acid, trifluoroacetic acid, camphorsulfonic acid, a polymer bound preparation thereof, a salt thereof, an aqueous solution thereof, and mixtures thereof, alone or in combination with methanesulfonic acid.

32. The process of claim 26 wherein the acidic solution comprises methanesulfonic acid.

33. The process of claim 26 wherein the compounds of Formula 2 and Formula 1a are combined in a ratio in the range of 2.5:1 to 3.2:1.

34. The process of claim 26 further comprising heating the compounds of Formula 1a and Formula 2 in the acidic solution at a temperature in the range of 85° C. to 95° C. for a time period of 1 to 16 hours.

35. The process of claim 34 wherein the compound of Formula 1a is in a mixture with Formula 1

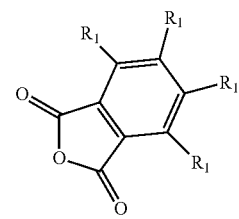

and the mixture is combined with two equivalents of the compound of Formula 2.

36. The process of claim 26 further comprising isolating the intermediate compound of Formula 3a.

37. The process of claim 36 wherein the isolating comprises suspension of the intermediate compound of Formula 3a, collection of the intermediate compound of Formula 3a, and rinsing the intermediate compound of Formula 3a with a substantially chloride-ion-free solvent.

38. The process of claim 37 wherein the solvent comprises a mixture of acetone and water heated to 60° C.

39. The process of claim 26 wherein the solution containing the intermediate compound of Formula 3a comprises less than 1500 ppm chloride.

40. The process of claim 26 further comprising heating the combined intermediate compound of Formula 3a and iodine in basic solution at a temperature in the range of 20° C. to 100° C. for a time period in the range of 1 to 24 hours.

41. The process of claim 40 further comprising heating the intermediate compound of Formula 3a and iodine in solution at a temperature in the range of 70° C. to 95° C. for a time period in the range of 1 to 24 hours.

42. The process of claim 26 wherein the solution of combined intermediate compound of Formula 3a and iodine comprises at least one base selected from the group consisting of sodium hydroxide, potassium hydroxide, lithium hydroxide, sodium bicarbonate, potassium bicarbonate, and mixtures thereof.

43. The process of claim 26 wherein the solution comprises sodium hydroxide at a concentration of 0.4 to 1.0 M.

44. The process of claim 26 further comprising adding at least one iodine-solubilizing agent to the solution comprising the combined intermediate compound of Formula 3a and iodine wherein the iodine-solubilizing agent is selected from the group consisting of potassium iodide, lithium iodide, sodium iodide, and mixtures thereof.

45. The process of claim 44 wherein the iodine-solubilizing agent comprises 1 to 2.5 equivalents of sodium iodide.

46. The process of claim 26 wherein iodine is generated in situ by adding to the solution containing the intermediate compound of Formula 3a an oxidizing agent and an iodide salt wherein the solution is substantially free of chloride ions, chloride-ion free radicals, hypochlorite, hypochlorous acid or mixtures thereof.

47. The process of claim 26 further comprising adding an iodine scavenger to the solution subsequent to the formation of the compound of Formula 3, wherein the scavenger is selected from the group consisting of sodium thiosulfate, potassium thiosulfate, ammonium thiosulfate, potassium sulfite, sodium sulfite and mixtures thereof.

48. The process of claim 47 wherein the iodine scavenger is sodium sulfite.

49. The process of claim 48 wherein the addition of iodine scavenger is performed at a temperature of 10° C. or lower.

50. The process of claim 26 wherein acidifying comprises adding a chloride-ion-free acid to the solution containing Formula 3.

51. The process of claim 50 wherein the chloride-ion-free acid comprises sulfuric acid at a concentration of 1 percent to 5 percent, and where this sulfuric acid is added in sufficient quantity to adjust pH of the solution to be in the range of pH 2 to pH 5.

52. The process of claim 51 wherein the pH is adjusted to approximately 3.

53. The process of claim 26 wherein the isolating comprises suspending the compound of Formula 3 in a solvent selected from the group consisting of water, dimethylformamide, acetone and mixtures thereof; vacuum filtration; and rinsing the resultant filter cake with a solvent selected from the group consisting of water, dimethylformamide, acetone and mixtures thereof.

54. The process of claim 26 wherein said compound of Formula 3, in which $R_1$ is independently Cl or Br, $R_2$, $R_3$, $R_4$, $R_5$ are I and $R_6$ is H, is converted to the quinoid form of Formula 4, wherein $R_{11}$ and $R_{12}$ are independently H or a counter-ion capable of forming a pharmaceutically acceptable salt

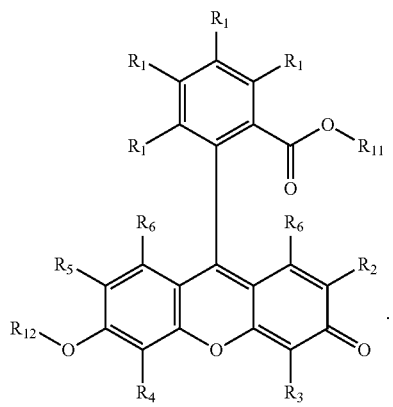

55. The process of claim 54 wherein $R_{11}$ and $R_{12}$ are sodium.

* * * * *